US008795730B2

(12) United States Patent
Vachon

(10) Patent No.: US 8,795,730 B2
(45) Date of Patent: Aug. 5, 2014

(54) COMPOSITIONS AND METHODS FOR PROMOTING THE HEALING OF TISSUE OF MULTICELLULAR ORGANISMS

(76) Inventor: David John Vachon, Spokane, WA (US)

( * ) Notice: Subject to any disclaimer, the term of this patent is extended or adjusted under 35 U.S.C. 154(b) by 441 days.

(21) Appl. No.: 12/690,081

(22) Filed: Jan. 19, 2010

(65) Prior Publication Data

US 2010/0247544 A1    Sep. 30, 2010

Related U.S. Application Data

(63) Continuation-in-part of application No. 12/162,990, filed as application No. PCT/US2007/002780 on Jan. 31, 2007.

(60) Provisional application No. 60/764,033, filed on Jan. 31, 2006.

(51) Int. Cl.
*A61K 9/00* (2006.01)
*A61K 9/06* (2006.01)
*A61K 9/08* (2006.01)
*A61K 31/795* (2006.01)

(52) U.S. Cl.
USPC ................. 424/486; 424/78.37; 424/78.38

(58) Field of Classification Search
None
See application file for complete search history.

(56) References Cited

U.S. PATENT DOCUMENTS

| | | | |
|---|---|---|---|
| 4,375,461 A | 3/1983 | Gander et al. | |
| 4,563,184 A | 1/1986 | Korol | |
| 4,725,271 A | 2/1988 | Korol | |
| 4,791,063 A | 12/1988 | Hon et al. | |
| 5,187,153 A | 2/1993 | Cordell et al. | |
| 5,196,196 A | 3/1993 | Scott et al. | |
| 5,488,160 A | 1/1996 | Morrissey | |
| 5,607,686 A | 3/1997 | Totakura | |
| 5,733,563 A | 3/1998 | Fortier | |
| 5,773,430 A | 6/1998 | Simon et al. | |
| 5,914,282 A | 6/1999 | Dunshee | |
| 5,972,366 A | 10/1999 | Haynes et al. | |
| 6,103,498 A | 8/2000 | Lawrence et al. | |
| 6,156,334 A | 12/2000 | Meyer-Ingold et al. | |
| 6,239,182 B1 | 5/2001 | Zaneveld et al. | |
| 6,326,359 B1 | 12/2001 | Monaghan et al. | |
| 6,326,421 B1 | 12/2001 | Lipman | |
| 6,407,156 B1 * | 6/2002 | Hagihara et al. | 524/494 |
| 6,537,538 B2 | 3/2003 | Zaneveld et al. | |
| 6,572,878 B1 | 6/2003 | Blaine | |
| 6,627,785 B1 | 9/2003 | Edwards et al. | |
| 6,703,013 B1 | 3/2004 | Ninomiya et al. | |
| 6,723,885 B1 | 4/2004 | Heydenreich et al. | |
| 6,892,890 B2 | 5/2005 | Dominguez | |
| 2002/0034491 A1 | 3/2002 | Fitzpatrick et al. | |
| 2002/0044941 A1 | 4/2002 | Rosen et al. | |
| 2002/0110585 A1 | 8/2002 | Godbey et al. | |
| 2003/0077301 A1 | 4/2003 | Maibach et al. | |
| 2003/0133991 A1 | 7/2003 | Monroe et al. | |
| 2003/0138397 A1 | 7/2003 | Kurtz et al. | |
| 2004/0126345 A1 * | 7/2004 | McNamara | 424/63 |
| 2004/0141936 A1 | 7/2004 | Kropke et al. | |
| 2004/0142910 A1 | 7/2004 | Vachon et al. | |
| 2005/0147581 A1 * | 7/2005 | Zamiri et al. | 424/78.27 |
| 2006/0068013 A1 | 3/2006 | Ditizio | |
| 2011/0097402 A1 | 4/2011 | Ditizio | |

FOREIGN PATENT DOCUMENTS

| | | |
|---|---|---|
| CA | 2 374 435 | 12/2000 |
| EP | 0099477 | 2/1984 |
| GB | 2433205 A | 6/2007 |
| WO | WO 81/02420 | 9/1981 |
| WO | WO 96/06893 | 3/1996 |
| WO | WO 97/00991 | 1/1997 |
| WO | WO 97/50143 | 12/1997 |
| WO | WO 99/51523 | 10/1999 |
| WO | WO 01/23514 | 4/2001 |
| WO | WO 01/70385 | 9/2001 |
| WO | WO 01/84244 | 11/2001 |
| WO | WO 02/49557 | 6/2002 |
| WO | WO 02/50000 | 6/2002 |
| WO | WO 03/024435 | 3/2003 |
| WO | WO 2004/000983 | 12/2003 |
| WO | WO 2004/021366 | 3/2004 |
| WO | WO 2004/092316 | 10/2004 |
| WO | WO 2004/112746 | 12/2004 |
| WO | WO 2005/073805 | 8/2005 |
| WO | WO 2006/098729 | 9/2006 |

OTHER PUBLICATIONS

Vachon et al (2006) J Biomed Materials Res Part A, 76A(1):35. WO PCT/US07/02780 Search Report, Dec. 4, 2007, David John Vachon.
WO PCT/US07/02780 Search Report, Dec. 4, 2007, David John Vachon.

(Continued)

*Primary Examiner* — Robert A Wax
*Assistant Examiner* — Jessica Worsham
(74) *Attorney, Agent, or Firm* — Wells St. John P.S.

(57) ABSTRACT

Compositions are provided for promoting healing of tissue of a vertebrate organism. The compositions can be for internal administration of a therapeutically effective amount of pharmacologically active, protease inhibiting, aqueous media soluble polysulfonated materials in salt form and associated with a secondary material to reduce one or more of inflammation, bacterial proliferation, proteolytic activity, and cancerous cell growth. The compositions may additionally or alternatively be cross-linked so as to alter the solubility of these pharmacologically active salts or slow dissolution by providing biodegradable cross-linkers. Compositions for healing the tissue of a multicellular organism are provided that can include a polysulfonated material in a liquid mixture, as solid particles or constructs that may or may not biodegrade or deliver a pharmacologically relevant value. Some of the compositions are also provided for inclusion into a device for preventing infection, reducing inflammation, and preserving the activity of a protein or protein drug.

14 Claims, 19 Drawing Sheets

(56) References Cited

OTHER PUBLICATIONS

WO PCT/US07/02780 Written Opinion, Dec. 4, 2007, David John Vachon.
GB 0815632.5 Examination Report, Apr. 6, 2010, Vachon.
WO PCT/US2007/02780 IPRP, Aug. 14, 2008, Vachon.
Anderson, et al., "Evaluation of Poly(Styrene-4-Sulfonate) as a Preventive Agent for Conception and Sexually Transmitted Diseases," Journal of Andrology, vol. 21, No. 6, pp. 862-875.
Garg, et al., "Compendium of Pharmaceutical Excipients for Vaginal Formulations".
Liekens, et al., "Modulation of Fibroblast Growth Factor-2 Receptor Binding, Signaling, and Mitogenic Activity by Heparin-Mimicking Polysulfonated Compounds", Molecular Pharmacology, 56, 204-213.
http://dictionary.reference.com/browse/associate as cited on Jul. 5, 2012.

* cited by examiner

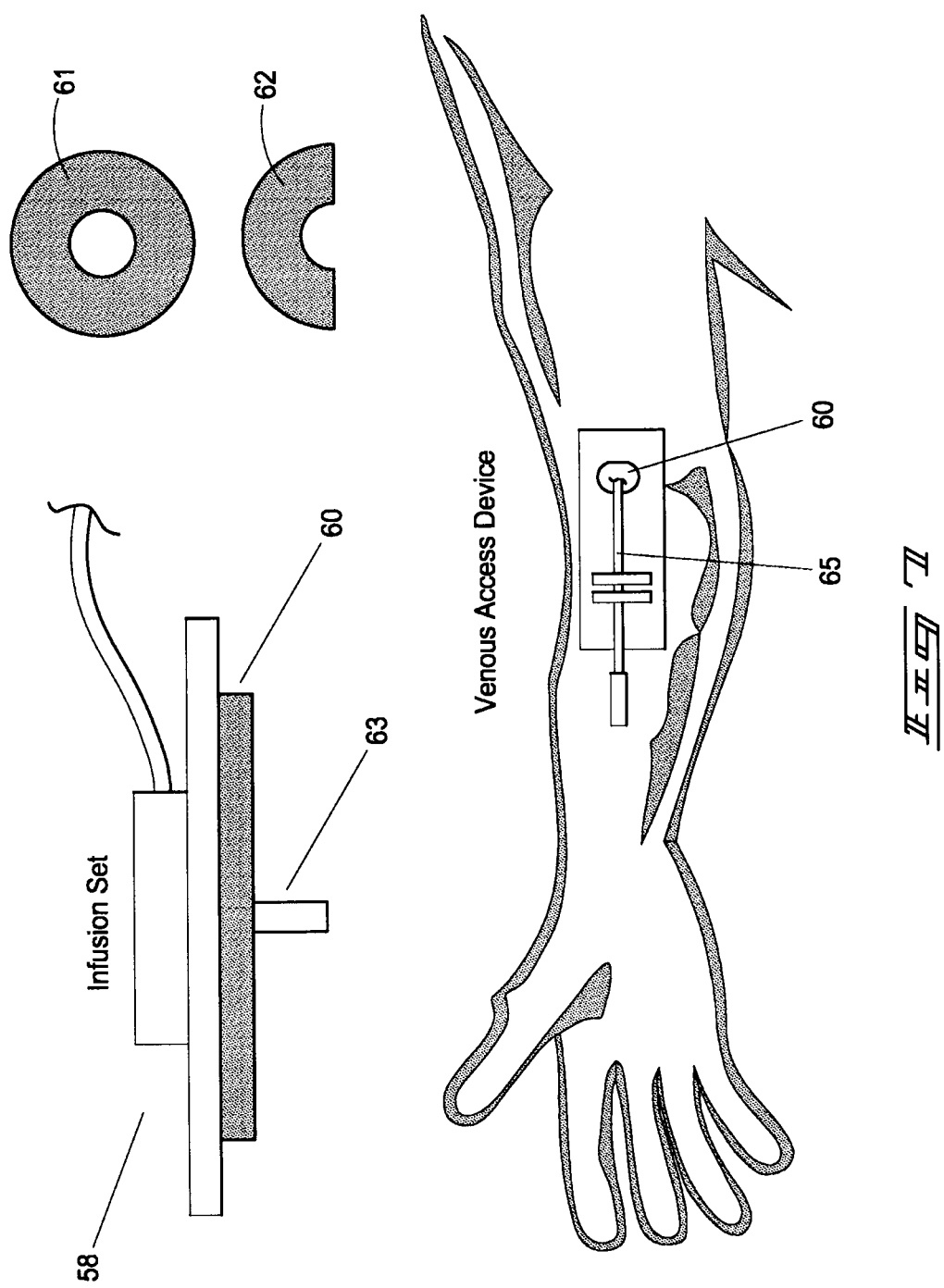

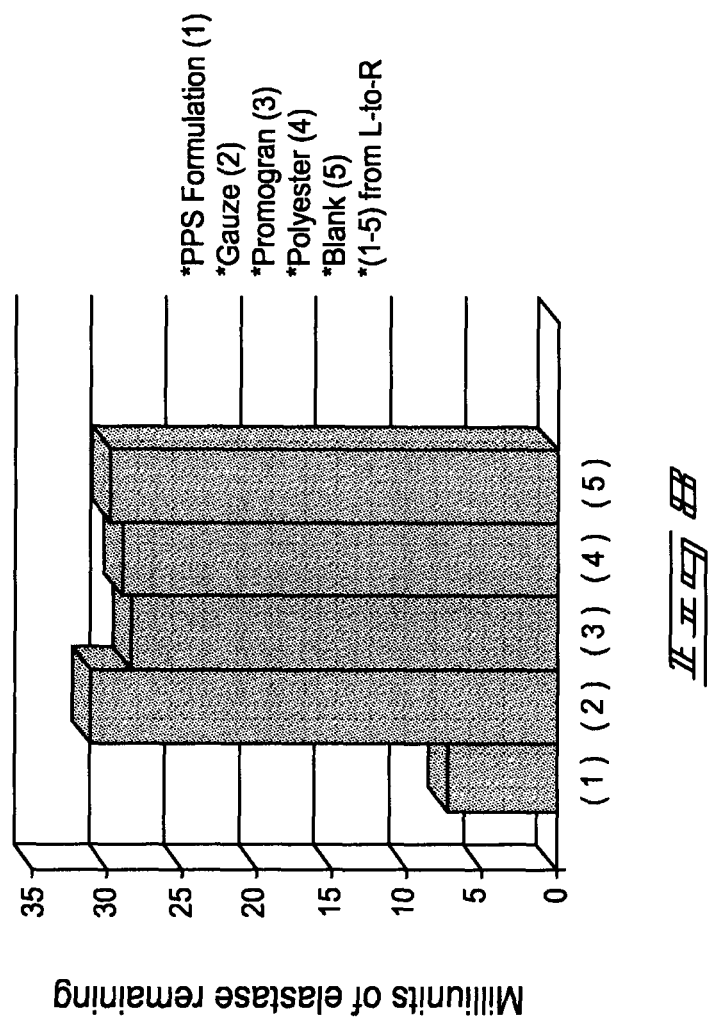

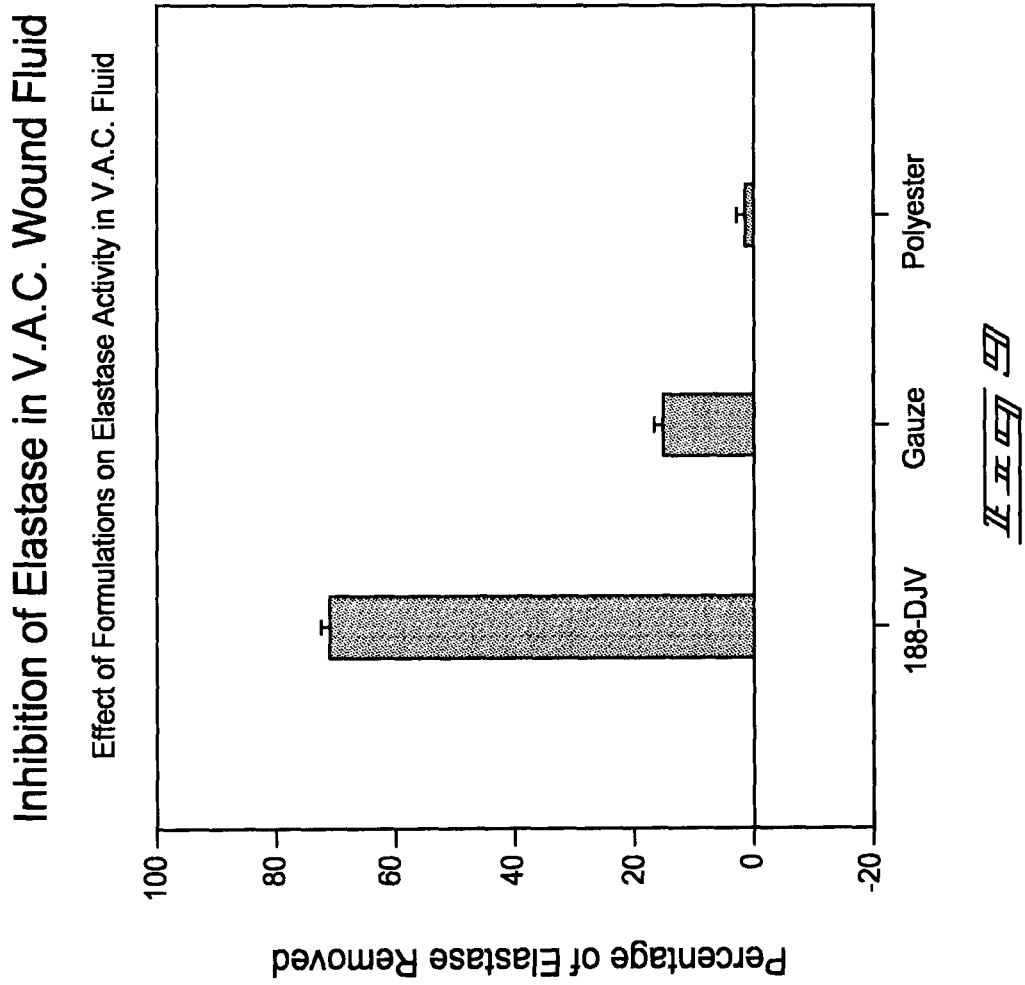

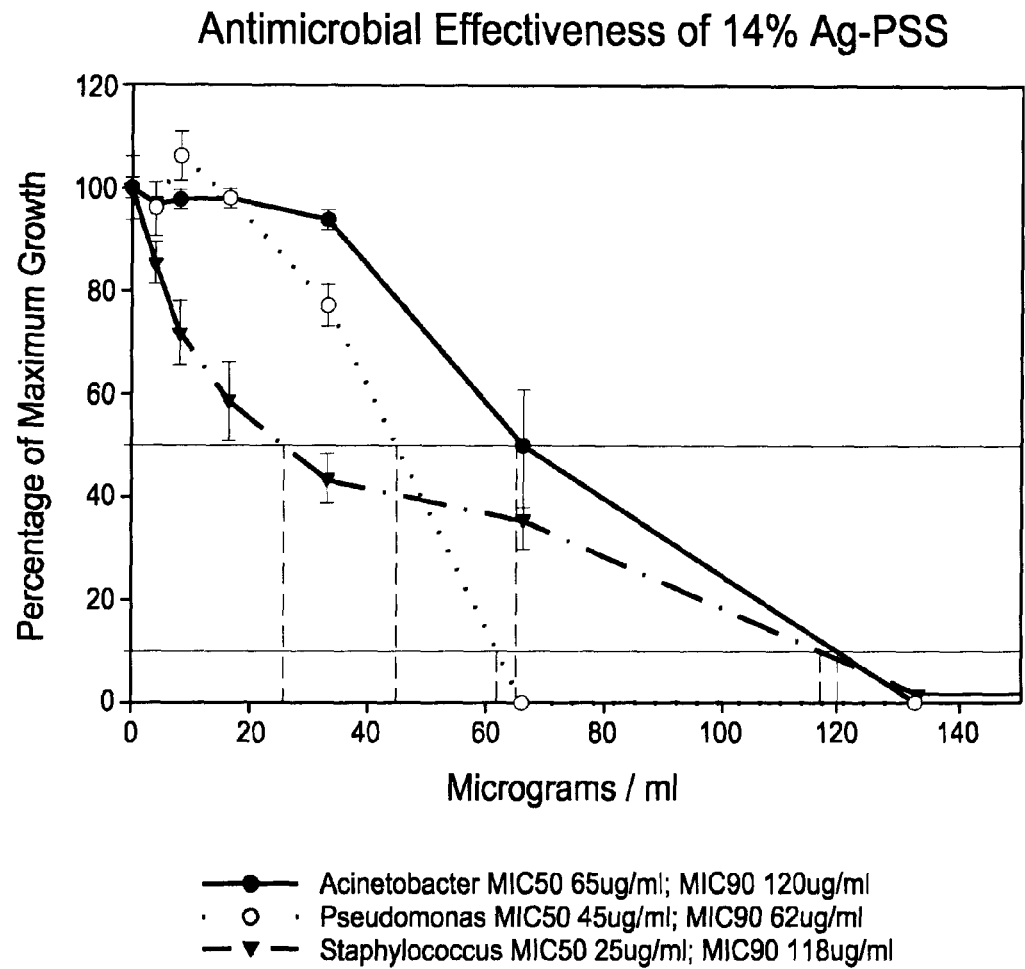

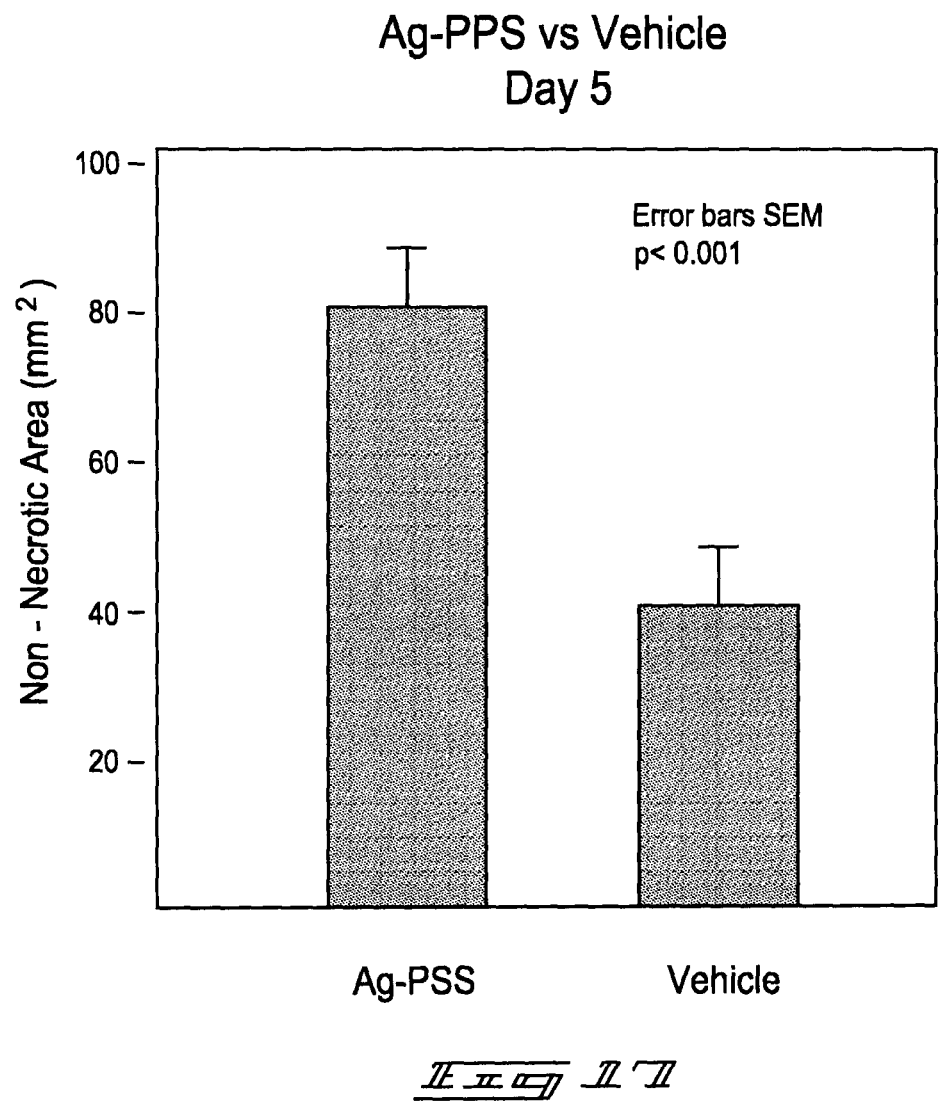

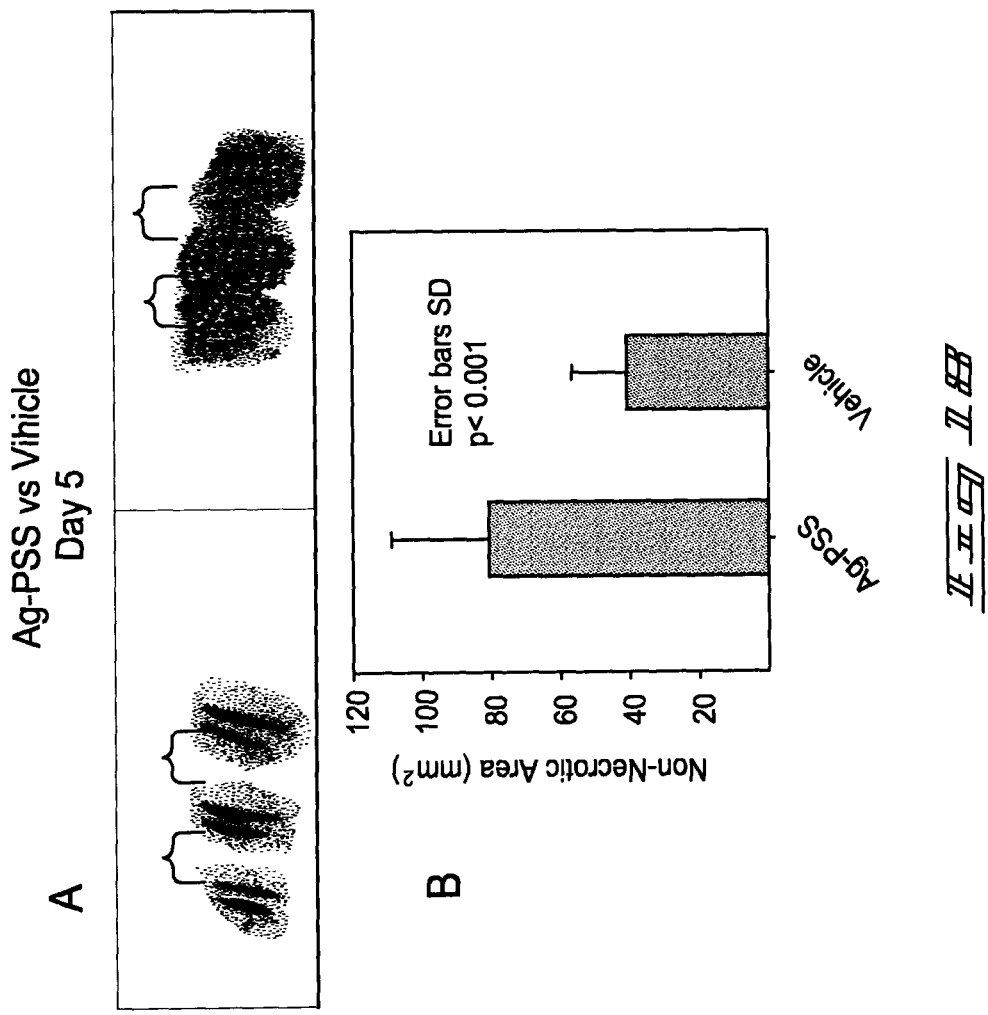

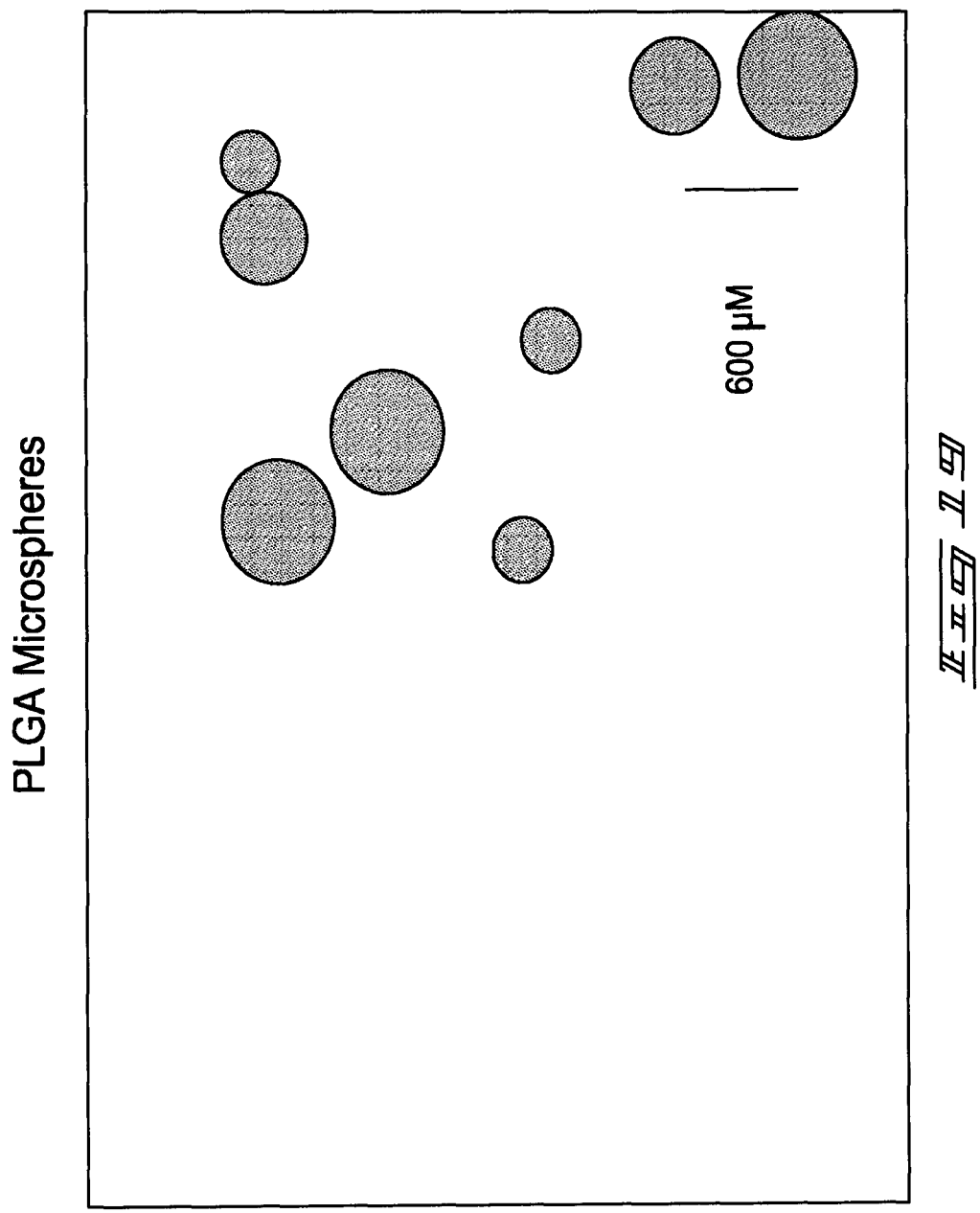

COMPOSITIONS AND METHODS FOR PROMOTING THE HEALING OF TISSUE OF MULTICELLULAR ORGANISMS

RELATED APPLICATIONS

This application is a continuation in part of, and claims priority to, U.S. patent application Ser. No. 12/162,990 filed 2008 Jul. 31 claiming priority to International Patent Application No. PCT/US07/02780 filed 2007 Jan. 31, both of which claim priority to U.S. Provisional Patent Application Ser. No. 60/764,033 entitled "Method For The Reduction of Protease Levels and Delivering Cationic Therapeutic Agents Using Water-Soluble Polyanionic Oligomers & Polymers & Their Salts" filed 2006 Jan. 31. The present patent application hereby incorporates each of these listed patent applications by reference in their entirety.

TECHNICAL FIELD

Compositions and methods for promoting the healing of tissue of multicellular organisms.

BACKGROUND

The biochemical environment of the non-healing wound (as well as serious wounds, including infected wounds, and/or chronic wounds) is different from that of the normal healing wound in ways that negatively affect multiple aspects of the healing process.

In each wound, one of the three mechanisms can predominate. The three mechanisms of wound healing are contraction, epithelialization, and connective tissue deposition. Contraction is the method by which wound healing occurs at an amputation site such as the tip of a finger. Epithelialization can predominate in the healing of abrasions and connective tissue deposition occurs when lacerations are sutured closed. The stages of healing include hemostasis, inflammation, proliferation and remodeling. In each of these stages, specific components can play a part through several mediators. In hemostasis, platelets, endothelial cells, and fibrin, and fibronectin act in concert through mediation by various biological factors including cytokines. Cytokines are non-antibody proteins that are released from some cells and act as intracellular mediators. Cytokines include lymphokines and interleukins. Inflammation occurs through the action of neutrophils, macrophages and lymphocytes mediated by growth factors and proteases. Proteases are enzymes that lyse proteins and are also known as proteinases. Herein, proteinase and protease can be used interchangeably. Proliferation occurs through the actions of fibroblasts, epithelial, and endothelial cells and is largely dependent on growth factors and collagen deposition. Remodeling is characterized by collagen cross linking and collagen degradation increasing scar strength as maturation of scar formation occurs.

Normal wound healing can be considered a balance of damaged tissue removal and new tissue formation. Many processes are present that can regulate the biological processes and pathways associated with normal wound repair. An alteration in any of these physiological processes can lead to the formation of a chronic wound.

Inflammation and/or innate immunity are related to cancerous cell growth. Early in the neoplastic process, inflammatory cells and their released molecular species influence the growth, migration and differentiation of all cell types in the tumor microenvironment, whereas later in the tumorigenic process, neoplastic cells also divert inflammatory mechanisms, such as proteinase production, and chemokine/cytokine functions in favor of tumor spreading and metastasis. Human polymorphonuclear neutrophils (PMN) comprise 50-70% of circulating leukocytes and induce inflammatory reactions that can be either cytotoxic for tumor cells or aid in tumor growth and metastasis.

The present disclosure provides compositions and/or methods using compositions that can reduce one or both of inflammation and cancerous cell growth, inhibit bacterial organisms, and/or generally promote healing and wellness, among other potential advantages in multicellular organisms.

SUMMARY

Compositions are provided for promoting the healing of tissue of a multicellular organism. The compositions include pharmacologically active, protease inhibiting, aqueous media soluble polysulfonated materials in salt forms in a liquid or solid mixture to reduce one or more of inflammation, proteolytic activity, bacterial proliferation, and cancerous cell growth.

Compositions are also provided for promoting healing of tissue of a vertebrate organism. The compositions can be for internal administration of a therapeutically effective amount of pharmacologically active, protease inhibiting, aqueous media soluble polysulfonated materials in salt form and associated with a solid material to reduce one or both of inflammation and cancerous cell growth. The polysulfonated materials in salt form may also be cross-linked so as to alter the solubility of these pharmacologically active salts.

Compositions are also provided for inclusion into a device for preventing infection, reducing inflammation, and preserving the activity of a protein or protein drug where the device is constructed as a solid material which is associated with a drug delivery device or a biosensor.

FIGURES

FIG. 7 is a depiction of example applications according to an embodiment in the disclosure.

FIG. 8 refers to a preparation of material 18 (Tecophilic Polyurethane film containing sodium polystyrene sulfonate/SPSS) and refers to the inhibition of Elastase by SPSS versus controls.

FIG. 9 refers to a preparation of material 18 (DJV-188—ointment containing sodium polystyrene sulfonate/SPSS) and refers to the inhibition of Elastase by SPSS versus controls.

FIG. 10 refers to a preparation of material 18 (DJV-188—ointment containing sodium polystyrene sulfonate/SPSS)

and two different molecular weights of pure SPSS and refers to the inhibition of Elastase by SPSS versus controls (Nuggets & Gauze).

Figure 11:
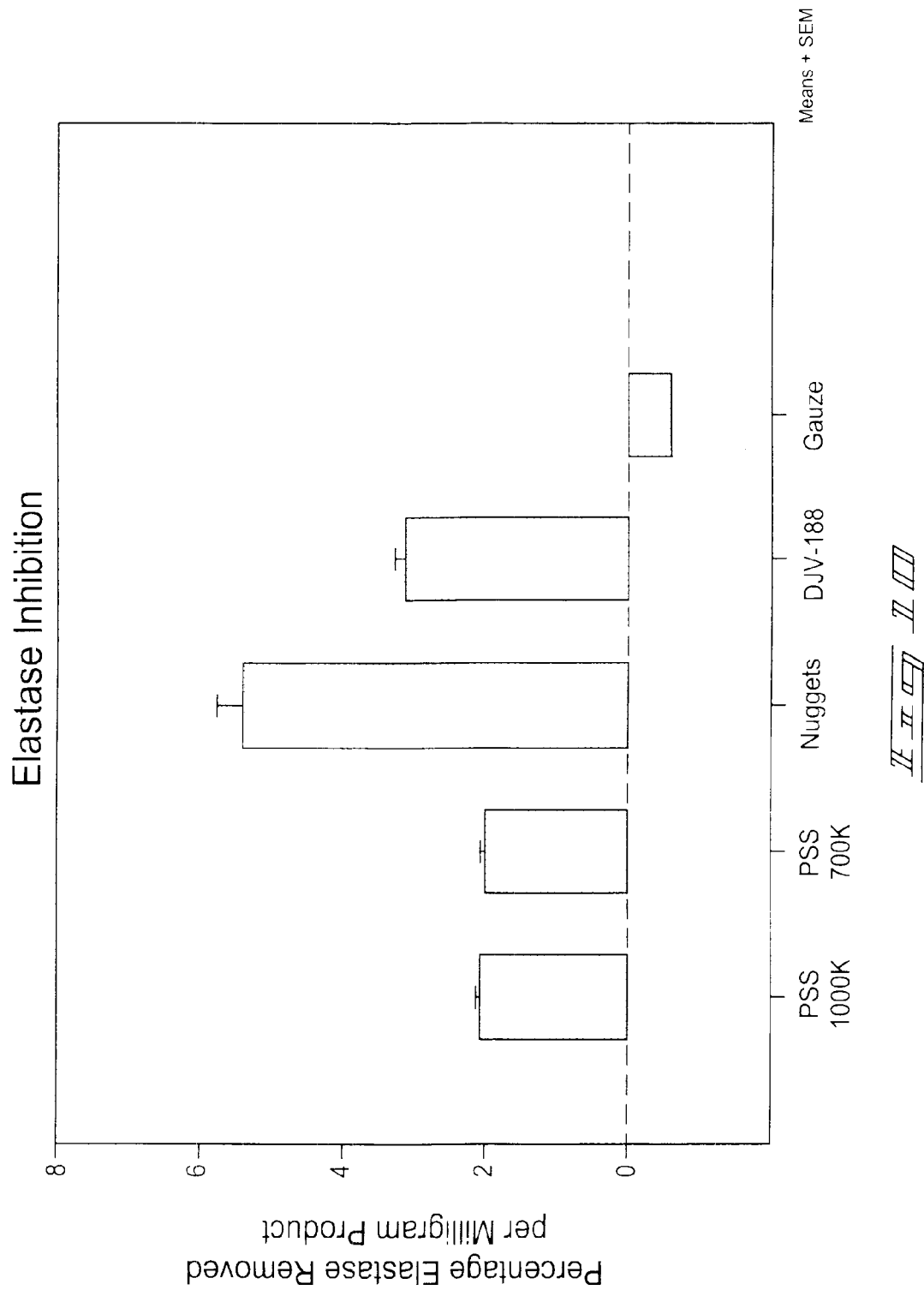
Figure 11:
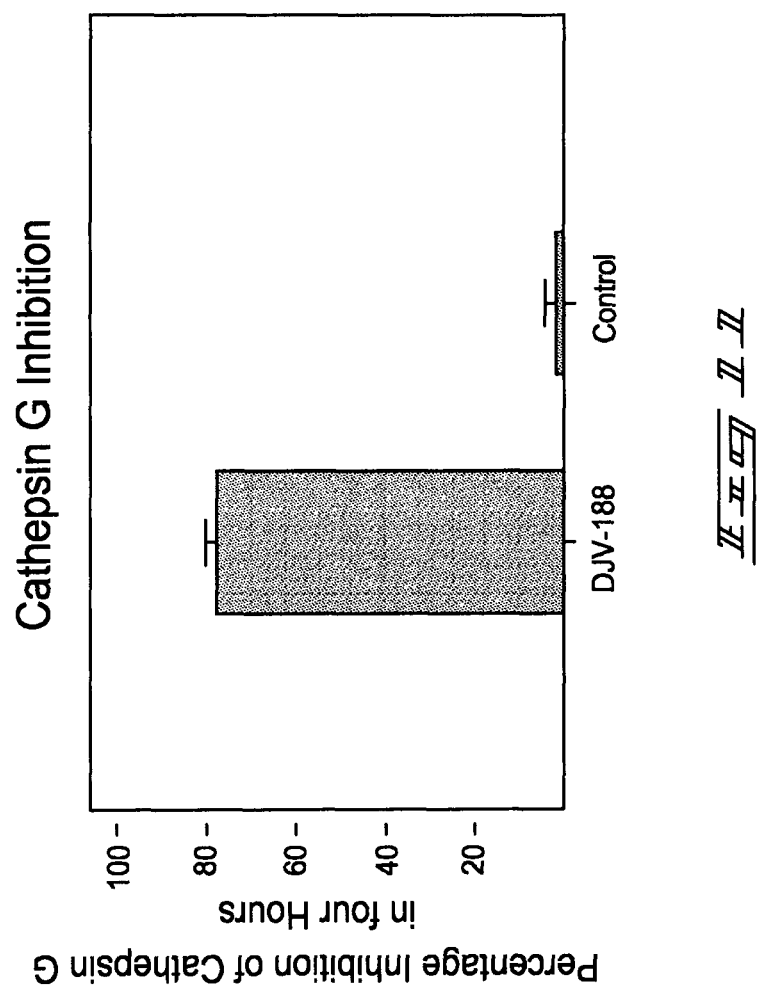

FIG. 11 refers to a preparation of material 18 (DJV-188—ointment containing sodium polystyrene sulfonate/SPSS) and refers to the inhibition of Cathepsin G by SPSS versus controls.

Figure 12:
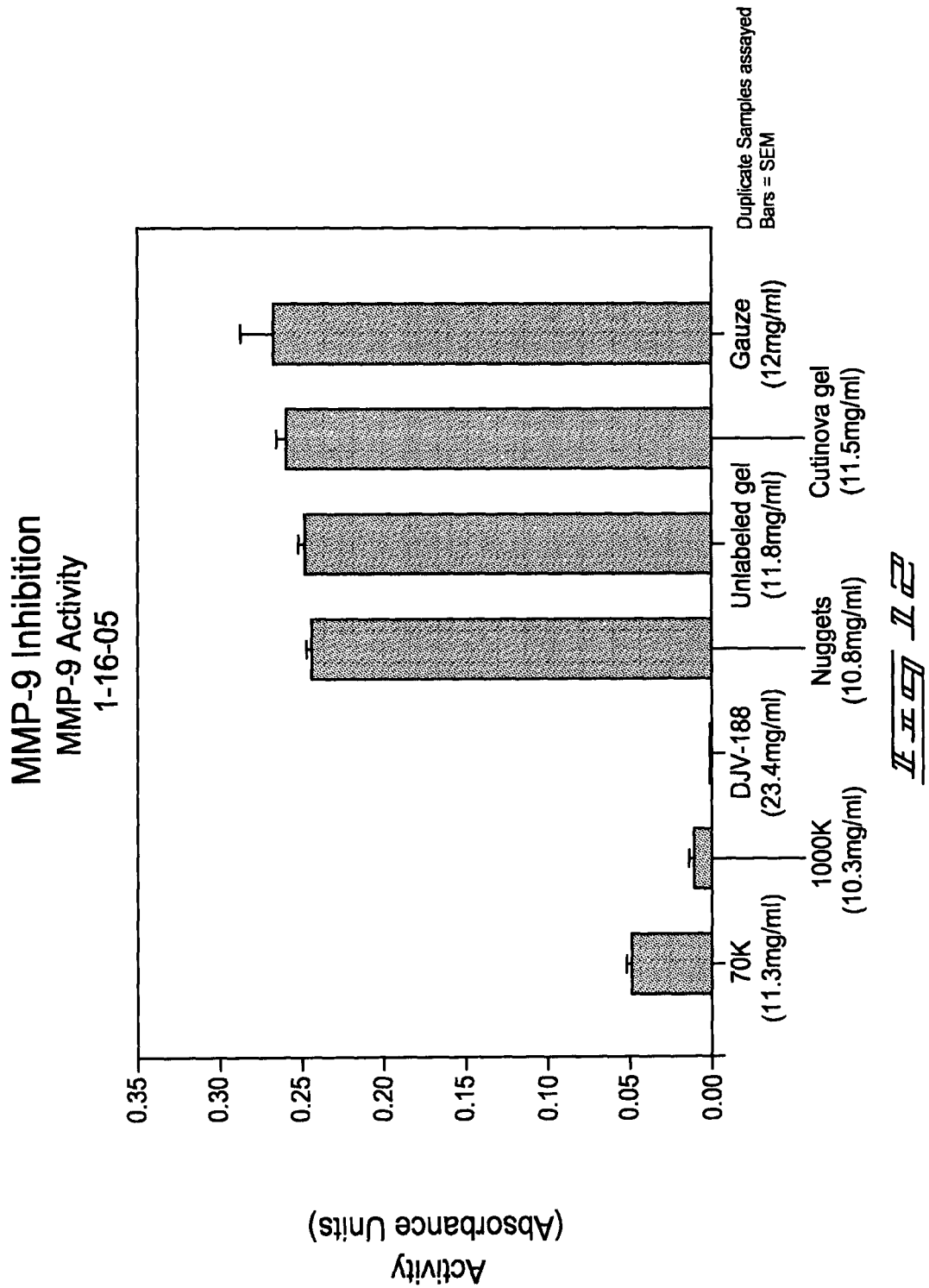

FIG. 12 refers to a preparation of material 18 (DJV-188—ointment containing sodium polystyrene sulfonate/SPSS) and two different molecular weights of pure SPSS and refers to the inhibition of MMP-9 by SPSS versus controls (Nuggets, unlabeled gel, Cutinova gel, & Gauze).

Figure 13:
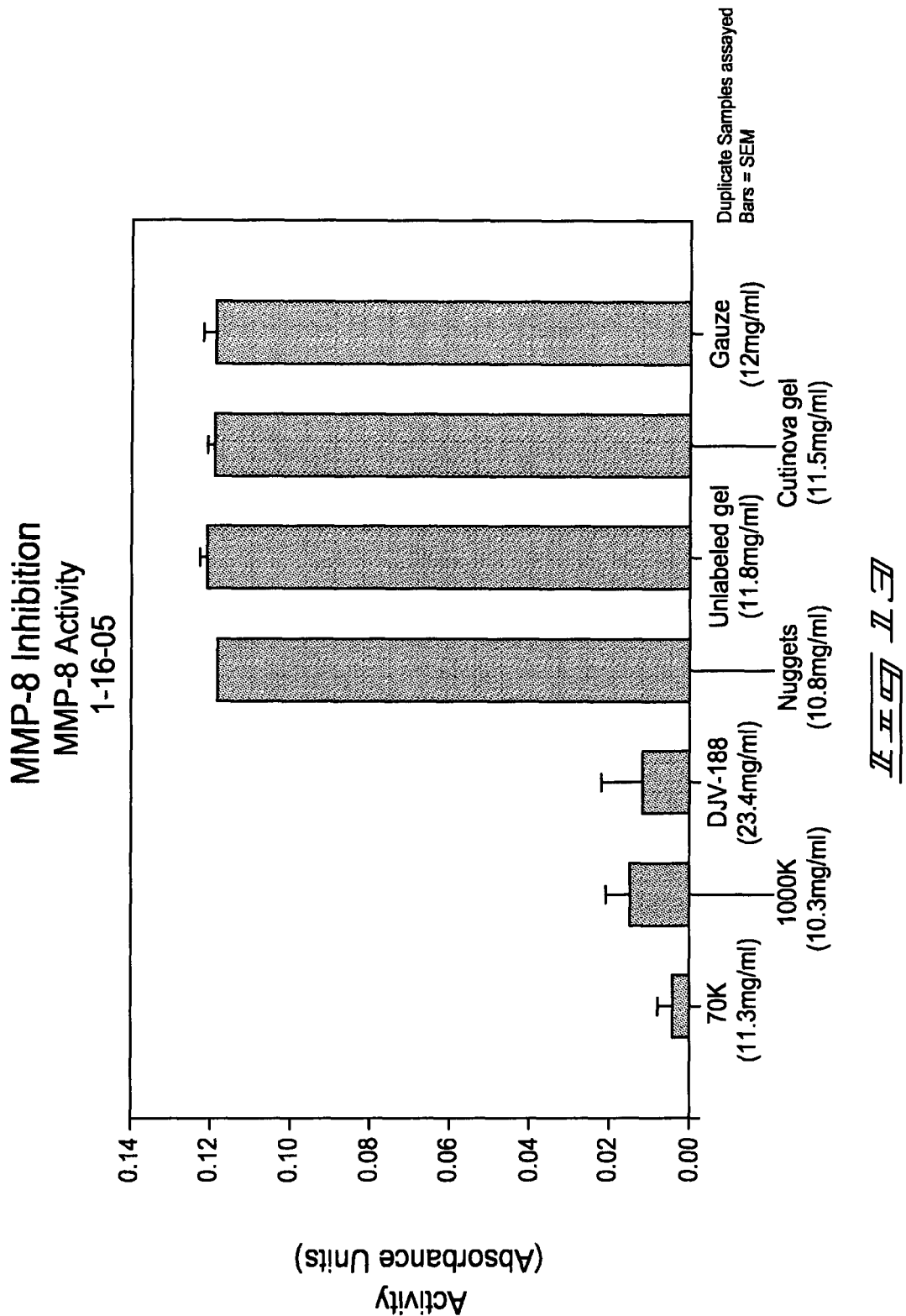

FIG. 13 refers to a preparation of material 18 (DJV-188—ointment containing sodium polystyrene sulfonate/SPSS) and two different molecular weights of pure SPSS and refers to the inhibition of MMP-8 by SPSS versus controls (Nuggets, unlabeled gel, Cutinova gel, & Gauze).

Figure 14:
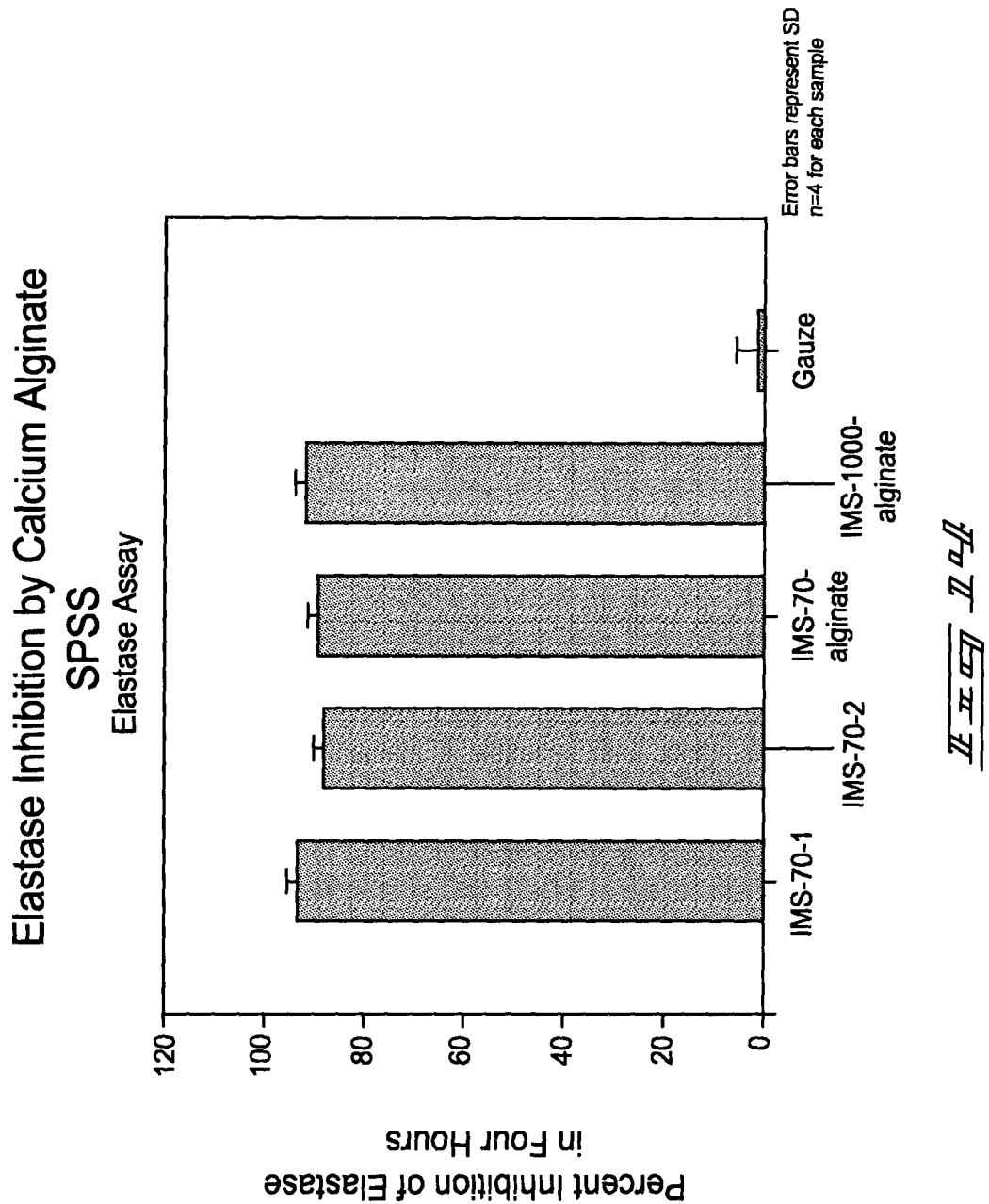

FIG. 14 refers to a preparation of material 18 (Calcium alginate film containing (calcium) polystyrene sulfonate of two different molecular weights) and two different solution preparations and refers to the inhibition of Elastase by (calcium) PSS versus controls (gauze).

Figure 15:
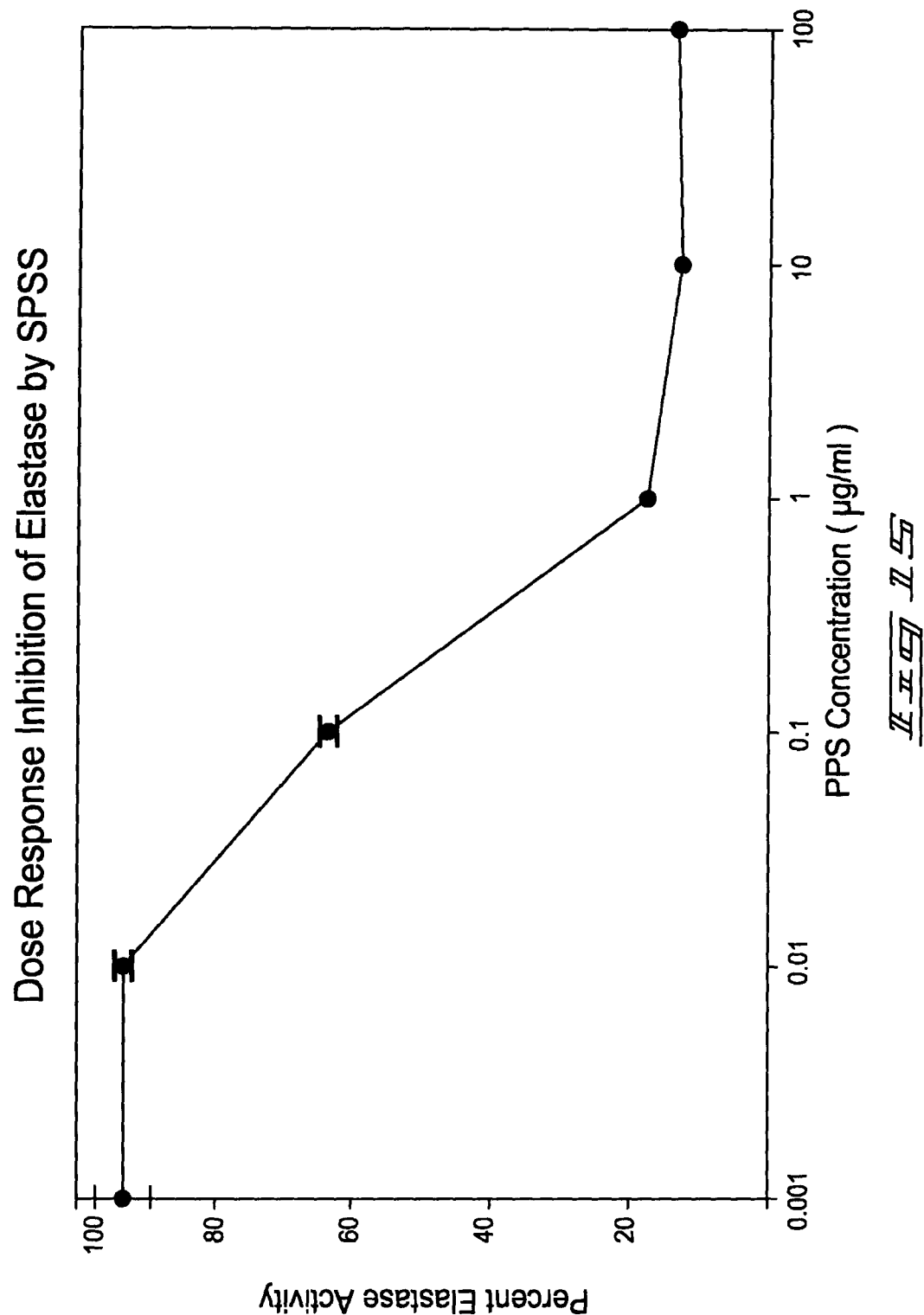

FIG. 15 refers to a dose response curve for SPSS in relation to its ability to inhibit a fixed amount of Elastase.

FIG. 16 refers to the ability of a mixed silver-sodium derivative of polystyrene sulfonate (14% silver) to kill three relevant bacterial organisms.

FIG. 17 refers to the healing benefit/results from a wound healing study where an example of material 18 (a mixed sodium-silver derivative of PSS (14% silver) compounded into an vehicle/ointment) was compared to a control (vehicle only).

FIG. 18 demonstrates application of material of the present disclosure to full thickness burn injuries.

FIG. 19 refers to the preparation of material 18 (SPSS compounded into PLGA microspheres).

DESCRIPTION

Figure 1:
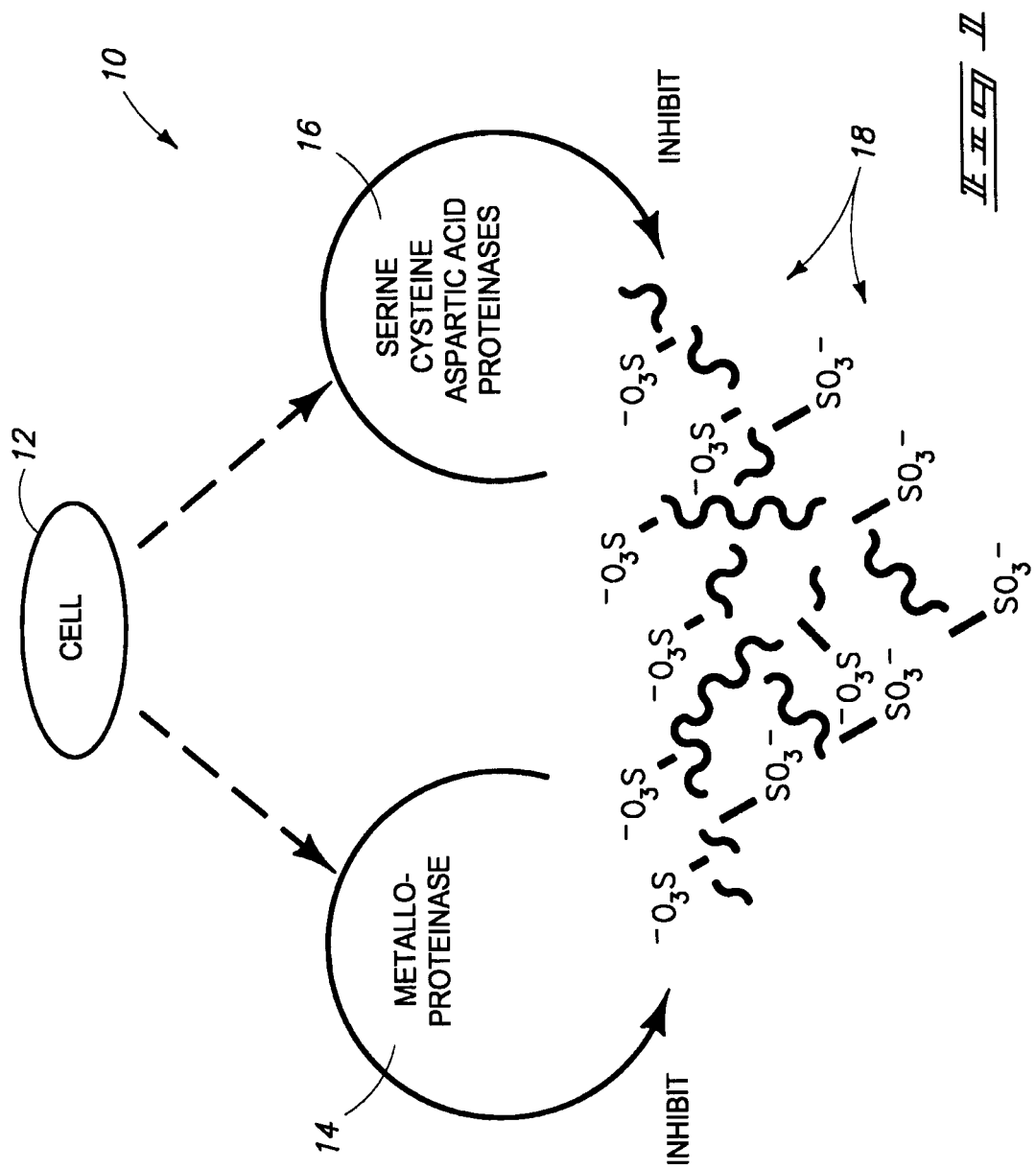
FIG. 1 is an example depicting the interaction of compositions of the disclosure with various proteinases produced by neutrophils and other cells according to an embodiment of the disclosure.

Compositions and methods of the present disclosure will be described with reference to FIGS. 1-18. Referring to FIG. 1, a general proteinase inhibition scheme 10 is shown that includes a cell 12 producing a metalloproteinase 14 and a serine, cysteine, or aspartic acid proteinase 16. Scheme 10 further includes the inhibition of proteinases 14 and 16 by a polysulfonated material 18. It is understood that several different proteinases may be inhibited (serine, cysteine, aspartic acid, & metallo-proteinases) and generally those proteinases (proteins) with high isoelectric points where at physiologic pH the overall positive charge on the protein provides the basis for a strong electrostatic interaction with the highly anionic polysulfonated material.

Figure 6:
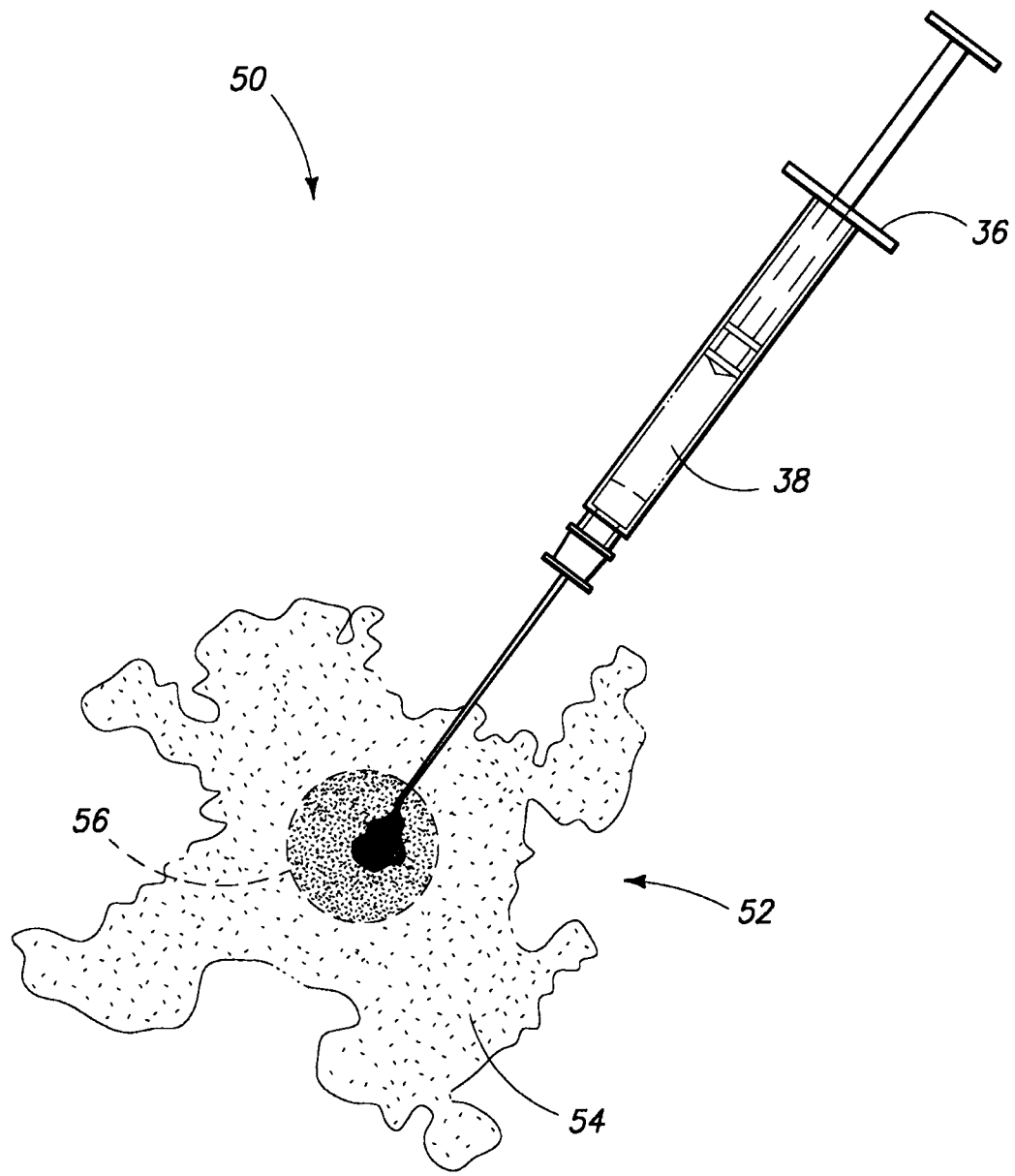
FIG. 6 is a depiction of an example application according to an embodiment of the disclosure.

The polysulfonated therapeutic compounds (material 18) described in this application represent a new class of natural, semisynthetic, or synthetic polysulfonated proteinase inhibitors (i.e. drugs) of both high isoelectric point proteinases and metalloproteinases without the need for additional proteinase inhibitor compounds. The effectiveness of the polysulfonated compounds is reflected in the examples and in the case of the ability of the water-soluble material 18 (Sodium polystyrene sulfonate, SPSS) to very effectively inhibit MMPs 8 & 9. FIG. 6 of this application describes the assay of water-soluble polysulfonated materials against MMP-8 and demonstrates the unexpected results that the water soluble material 18 (SPSS) is significantly more effective at inhibiting elastase than the non-water soluble strong cation exchange material (nuggets) and that the water soluble material 18 (SPSS) is remarkably effective against MMPs 8 & 9 whereas the non-water soluble strong cation exchange material is ineffective against MMPs 8 & 9. Furthermore, it was unexpected that the solubility of the polysulfonated materials described herein can be tailored to be completely insoluble in deionized water yet soluble in aqueous media.

Polysulfonated material 18 (hereinafter referred to as "material 18") can be a polysulfonated material, a polysulfated material and/or a polysulfonic acid salt or a polysulfated material of acid or salt form thereof. In some instances, the repeating unit of material 18 may be represented chemically as $[R(SO_3^-X^+)_m]_n$ with m representing the number of sulfonates or sulfates within a repeating unit of a macromolecule and where n is at least one and m is greater than 1. The R group contains carbon, hydrogen, and may possess other atoms including heteroatoms such as nitrogen, sulfur, and oxygen. "X" can be one or more variable cations including metal and organic species and may comprise mixtures of metal cations, organic cations or mixed metal cation-organic cation combinations. When the R group of material 18 is a repeating unit of a polymeric material, for example a polysaccharide, it is understood that the R group possesses an oxygen atom that is covalently linked between the ring (carbon) of the sugar and the $SO_3^-X^+$ functionality. As such, it is understood that the sulfonate groups of material 18 are associated with either counter cations or protons ($H^+$) in order to maintain nature's law of neutrality.

Sulfated polysaccharides, such as glycosaminoglycans are generally in their subsequent sodium salt forms and are generally highly water-soluble. Given the water solubility of these compounds, ion exchange to substitute other metal cations or organic cations for sodium can be readily accomplished using a variety of methods including for example the use of water-insoluble weak cation exchange resins.

While these counter ions are not shown in FIG. 1, it is understood that they are involved in the molecular architecture. The R group can be the backbone of an oligomer, such as a dimer and/or trimer, or a polymer, also known as a macromolecule for example. In accordance with other implementations, the oligomer or polymer can comprise monomeric units of arylenevinyl sulfonate, styrene sulfonate, alkyl styrene sulfonate such as methyl styrene sulfonate, sulfated saccharides, and/or vinyl sulfonate monomers as well as nonsulfonated monomers. The oligomer can include repeating units of the same monomer, or more than one monomer where the monomer may be chiral, achiral or a racemate. A racemate, or racemic mixture, is the result of having a mixture of chiral enantiomers each of which have chiral centers that are in essence mirror images of each other. In some cases, one enantiomer can have biological activity and its mirror image will not. In cases where more than one chiral center is involved, diastereomers can result. Diastereomerism occurs when two or more stereoisomers of a compound have different configurations at one or more (but not all) of the equivalent (related) stereocenters and are not mirror images of each other. Chirality, optical activity, and thus biological activity may be associated with the backbone structure, such as with polysaccharides or chirality may be induced in typically achiral materials by adding pendant chiral groups, i.e. those groups that possess typically one connecting point to the backbone (suspended from) and not critical to the connectivity of the backbone, or by modifying the aromatic (aryl) ring of an polyarylenevinyl sulfonate (aryl ring-modified) to include a chiral group. Chirality is typically measured by an optical activity (rotation of plane-polarized light) whereby the light is rotated clockwise or counterclockwise.

The literature describes polymeric (water insoluble) medical materials that possess protease inhibition capabilities. In some instances water-insoluble polycationic ion exchange ligands are used and in other instances polyanionic ion exchange (hydrogel) materials are described for aiding in wound healing. The materials discussed in the literature are configured with a variety of chemistries and include phosphoryl groups, sulfonate groups, and quaternary ammonium groups in addition to biopolymers that include collagen. Several of these materials target neutrophil elastase and the collagenase MMP-8 and gelatinase MMP-9. Of all of the above mentioned chemistries, the biopolymers are not true inhibitors of proteinases and only compete for the analyte in the assays. The insoluble strongly anionic dressings are effective against elastase but ineffective against the metalloproteinases (MMP-8 & MMP-9) unless a tetracycline is used in addition.

According to an example implementation, the oligomer can be incorporated into other materials. For example, material 18 can also be a polymer comprising the oligomer. The oligomer can be copolymerized with other monomers and/or other oligomers to form a copolymer. In accordance with embodiments of the disclosure, the polymer can include repeating oligomeric units, where the oligomeric units may be comprised of identical monomer units or combinations of monomer units. For example, material 18 can be polyarylenevinyl sulfonate, polystyrene-sulfonate, polymethylstyrene-sulfonate polyvinylsulfonate, polyantholesulfonate, and/or acrylamidomethyl propane sulfonate polymer, among others.

Accordingly, polysulfonated material 18 may be synthesized by polymerization of one or more sulfonated monomers or by sulfonation of a synthetic or semi-synthetic polymer or sulfation of a synthetic, semi-synthetic, or naturally occurring polymer such as a polysaccharide. The sulfonated or non-sulfonated monomers that eventually lead to material 18 being sulfonated may be chiral, achiral (non-chiral), or racemic mixtures or combinations thereof. In the case of a chiral monomer (either sulfonated or non-sulfonated) that is polymerized, the resulting polymer can be chiral (i.e. it does not possess a plane of symmetry or cannot be superimposed over its mirror image) and can be optically active. In the case of the non-sulfonated monomer, sulfonation post polymerization can be carried out. The resulting material may possess unique properties that allow specific interactions with biologically active species such as observed for glycosaminoglycans some of which are known to possess a "sulfation code". This sulfation code can allow for the polysulfonated material to protect biological species necessary for good healing and repair. In some cases, the sulfation code can be designed into a synthetic polysulfonated compound by the inclusion of chemical functionalities that allow the material 18 to interact favorably with biological molecules such as peptides, growth factors, cytokines and the like.

In another example, the presence of small amounts of material 18 can provide protection for protein therapeutic agents, such as insulin, from being degraded by enzymatic processes which can render these proteins ineffective and potentially proinflammatory to the site at which the drug is being delivered. In one example, a solid polymeric sheet containing polysulfonated material 18 is fabricated from a biomedical material such as a silicone gel and the solid sheet is positioned to surround a transcutaneous access point through which a medical device such as an infusion set makes contact with a patients tissue. The solid polymeric sheet, for example, can be formulated with an antibacterial, protease inhibiting, aqueous media soluble, polysulfonated material in salt form in order to protect the wound from invading microorganisms, thus preserving the viability of the subcutaneous tissue for the uptake of drug, and to preserve the drug by preventing degradation of the protein by proteases such a neutrophil elastase. Neutrophil elastase is known to lyse proteins at alanine-valine peptide bonds, among others. The alanine-valine peptide linkage is present in insulin thus rendering it susceptible to degradation. The protease inhibiting characteristics of material 18 can provide protection against this kind of degradation for example.

It is important to note that the use of an aqueous media-soluble polysulfonated material to prevent infection is not limited to a solid sheet configuration and may be formulated as a coating that may be provided directly on a medical device such as a transcutaneous infusion set or a glucose sensor. It is further understood that an antimicrobial agent alone, such as chlorhexidine, in such a device alone without a formulation to include a polysulfonated material may provide protection against invading pathogens and as such may increase the useful lifetime of use devices such as glucose sensors and infusion sets.

Furthermore, the ability of material 18 in its sulfonated form to inhibit proteases (enzymatic species that can include other proteins that degrade proteins) can prevent certain biological species from degradation in environments where proteolytic activity is high. The charge on these enzymes when their overall charge is neutral (isoelectric point) and whether or not the activity of these enzymes is related to an active site containing metal cation such as $Zn^{++}$ are relevant to this application.

The isoelectric point, sometimes abbreviated to IEP, is the pH at which a particular molecule or surface is absent of any net electrical charge. Amphoteric molecules called zwitterions contain both positive and negative charges depending on the functional groups present in the molecule. The net charge on the molecule is affected by the pH of their surrounding environment and can become more positively or negatively charged due to the loss or gain of protons (H+). The IEP is the pH value at which the molecule carries no electrical charge, where the negative and positive charges are in balance. Surfaces naturally charge to form a double layer. In biological systems, the surface charge-determining ions are hydronium ($H_3O^+$), and hydroxide ($OH^-$), counter ions that can include chloride ($Cl^-$), as well as metal cations that include sodium ($Na^+$) and potassium ($K^+$) for example. The net surface charge is affected by the pH of the medium/liquid surrounding the species of interest. The IEP value can affect the solubility of a molecule at a given pH. Such molecules have minimum solubility in water or salt solutions at the pH which corresponds to their IEP and often precipitate out of solution. Biological amphoteric molecules like proteins (polyaminoacids also known as polypeptides) contain both acidic and basic functional groups. The amino acids which make up proteins may be positive, negative, neutral or polar in nature, and together give a protein its overall charge.

At pH values below their IEP, proteins carry a net positive charge; above their isoelectric point the proteins are deprotonated and carry a negative charge. Proteins (including proteases) that have high isoelectric points (>7.5) are to some degree cationic (positively charged) at physiologic (neutral) pH (7.0). The higher the IEP, the more positive character the protein will possess at pH=7.0.

For the purposes of this application, examples of proteinases that are of merit and interest to inhibit can include aspartic acid, cysteine, metallo-, and serine proteinases, among others.

Sulfonate groups have a high affinity for cations, including multivalent cations such as $Zn^{++}$, $Ca^{++}$, and $Mn^{++}$ for example. In the case of a multivalent cation (≥charge of 2+), in order to satisfy the law of neutrality more than one sulfonate/sulfate group can interact with the cation or the cation may have other anions associated with it in addition to the sulfonate/sulfate groups.

The sulfonic acid group, in its acid form is a very effective cation exchange group and can exchange metal cations, for example, for protons. Thus, the $SO_3H$ moiety can interact with NaCl to form —$SO_3Na$ and HCl for example.

Material 18 can also include other sulfonated compounds such as, but not limited to, polymers of sulfated saccharides or polysulfated polysaccharides, such as dextrin sulfate, dextran sulfate, chitosan sulfate, or cellulose sulfate, among others. The sulfonate group of material 18 can be coupled directly to a structural unit depicted by —OR, with the R group representing the remainder of material 18, and the coupling to an oxygen atom {O} forming what is referred to as a sulfate group (—$OSO_3^-X^+$). Accordingly, sulfate groups contain sulfonate groups (—$SO_3^-X^+$). As such, material 18 can include polysulfonates including sulfonic acids, sulfonic acid salts, and polysulfated compounds, among others. The polysulfated compounds can include synthetic, semi-synthetic, and/or naturally occurring polysulfated polysaccharides that include chondroitin sulfate, heparan sulfate, heparin, or dextran sulfate given as an example above, as well as the sulfated semisynthetic polysaccharide pentosan polysulfate, for example. For instance, Sulfated polysaccharides, also known as glycosaminoglycans or GAGs, are efficient ion exchange materials by virtue of the sulfonate group present.

In some cases, material 18 can have a molecular weight of from about 600 grams/mole to about 1,000,000 grams/mole but may be in excess of 2,000,000 g/mole. As an example, material 18 can be a polymer or copolymer having a molecular weight of at least about 70,000 Daltons but may be less or more depending upon the application. Material 18 can also include polysulfonated material blended with another material. For example, polysulfonated materials such as polystyrenesulfonate can be blended with materials such as hydrogel(s). Hydrogels can include, but are not limited to, alginates, polyacrylates, polyalkylene oxides, and/or poly (N-vinyl pyrrolidone). The hydrogel may also be amorphous, i.e. a viscous gel as opposed to a solid such as a formulation of carboxymethylcellulose containing a humectant such as propylene glycol or glycerin. It is also possible to combine the components of material 18 in their separate forms into a liquid mixture for example allowing for the association to occur in the liquid or semisolid mixture such as an ointment comprising Petrolatum, Fatty Alcohol (stearyl), Emollient (isopropyl myristate), Emulsifying Agent (polyoxy (40) stearate, sorbitan monooleate), Humectant (propylene glycol), and sterile deionized water, among others. In this method the resulting association may result in a homogenous or heterogeneous formulation. Material 18 can also be blended with polyurethanes, for example. Material 18 can also be blended with naturally occurring polymers that include chitosan, hyaluronic acid, and starch, among others. Material 18 may additionally be covalently cross-linked with a diamine and a coupling agent. For example this may form a sulfonamide at some or all junctions where the diamine links to the sulfonic acid groups of material 18. In some cases, the cross-linking of the polysulfonated material can serve to alter the solubility of the polysulfonated material. The solubility is dependent upon the number of cross-link points introduced. Examples of cross-linkers can include peptides, aromatic or aliphatic diamines, diaminosaccharide and the like. Coupling agents can include 2-(1H-7-Azabenzotriazol-1-yl)-1,1,3,3-tetramethyl uronium hexafluoro phosphate (HATU), or O-Benzotriazole-N,N,N',N'-tetramethyl-uronium-hexafluoro-phosphate (HBTU), for example but may include pretreatment of the acid form of the polymer with thionyl chloride in order to yield the sulfonyl chloride which will react with an amine to form a sulfonamide. Furthermore, in cases where the cross-linker is a peptide sequence, one or more of the peptide bonds within the peptide may be designed to be susceptible to proteolytic cleavage. Peptides with the alanine-valine linkage would for example be susceptible to elastase cleavage. It is understood that MMPs such as MMPs 8 & 9 can cleave peptides at different peptide bonds. For example MMP-9 is known to cleave proline-proline and lysine-lysine bonds for example. As such, it is understood that these linkages can be built into the cross-linker in order to ensure that enzymatic degradation occurs thus leading to dissolution and essentially biodegradation of material 18. This feature would enable solubilization of the cross-linked material as the cross-links are cleaved (i.e. degradation of the linkage). Solubilization of the material can allow for the polysulfonated material 18 to function as a drug delivery vehicle or a gene delivery vehicle for example while providing some protease inhibitor characteristics. It is worth noting that if an amino compound with only one available amino group is added in the same fashion, partially modified sulfonamides can result. If the amine is a peptide, for example, a protease inhibitor with additional biological activity can result.

The $SO_3^-$ group can be referred to as a sulfonate group. The sulfonate group can be a terminal sulfonate group, and material 18 can include at least one terminal sulfonate group. In accordance with embodiments of the disclosure, the $SO_3^-$ groups of the polysulfonated material can extend from the oligomer backbone, such as a polymer or copolymer backbone.

The sulfonate group can take the form of an acid, for example. As an acid, the sulfonate group can be protonated, such as $SO_3H$. Material 18 can include many sulfonate groups and these sulfonate groups may all be protonated or some may be protonated while others are unprotonated depending upon the degree of substitution. According to another embodiment of the disclosure, the sulfonate groups of material 18 may be a component of a salt, such as a metal or organic salt. According to embodiments of this configuration, material 18 can be referred to as a polyanionic salt, such as polymetallosulfonate and/or a polyorganosulfonate. The sulfonate group of material 18 can be associated with either or both of an inorganic or organic element or compound that may be of pharmacologically relevant value. Pharmacologically relevant metal ions and organic ions are understood to be of value in treating at least one element of a medical condition. One such example is a bacterial infection which may be treated by an antibiotic compound such as a tetracycline, or a metal ion such as silver ion. As such it is understood that a polysulfonate may be substituted with more than one individual cationic species and may be either organic, inorganic (metal), or mixed organic-inorganic varieties.

Material 18 may also comprise a synthetic, semisynthetic, or biological polymer having at least one sulfonyl group extending from the polymer backbone. In one embodiment, a sulfonyl group is terminal. Examples include association of this sulfonyl group with an amino acid or as a component of a salt wherein the salt is a combination of the polyanionic sulfonate combined with an organic cation, where the organic cation can be for example one or more, but not limited to tetracycline, doxycycline, minocycline, gentamicin, arginine, linear and cyclic peptides, lysine, carnosine, glutathione, chlorhexidine, polyhexamethylenebiguanide, the cytotoxic chemotherapeutic agent doxorubicin, or lidocaine, among others. Thus, material 18 may be a polyanionic salt. For example, as a polyanionic salt material 18 can be one or more of a polyanionic metal salt, a polyanionic organic salt, or a mixed polyorganic-polyanionic inorganic (metal) salt, among others.

In accordance with an implementation, the sulfonate group can be associated with a complimentary cation. As an example, the sulfonate group can be associated with an inorganic species such as one or more of a positively charged metal such as $Na^+$, $Ag^+$, $K^+$, $Li^+$, $Au^+$, $Ca^{++}$, $Zn^{++}$, $Mn^{++}$, $Mg^{++}$, $Fe^{++}/Fe^{+++}$, and/or $Ce^{+++}$. The sulfonate can also be associated with $NH_4^+$ or $NR_4^+$ where R represents an alkyl, aryl or alkyl-aryl substituent for example. According to another example, the sulfonate group can be associated with one or more organic species. Examples of such organic species can include nitrogen containing organic species such as, an amino acid, a tetracycline, doxycycline, arginine, lysine, glutathione, lidocaine, albuterol, and/or alkyl/benzylammonium, among others.

In accordance with an example implementation, material 18 can be sodium polystyrene sulfonate (SPSS), a neutralized derivative of the corresponding polystyrene sulfonic acid. Sodium polystyrene sulfonate (SPSS) is a pharmacologically active compound used in the treatment of hyperkalemia. Sodium polystyrene sulfonate, (SPSS, sold as Kayexalate, Kalexate, or Kionex powder), is an anionic polymer commonly used in the treatment of hyperkalemia (high levels of potassium in the blood) and occasionally used in pharmaceutical formulations as an inert ingredient. As a treatment for hyperkalemia, PSS is taken either by mouth or enema and its action as a strong cation-exchange resin (highly anionic) removes excess potassium in these patients by exchange for the available sodium (via a metathesis exchange reaction of sodium for potassium) from the blood across the highly vascularized large intestine. The same result can be achieved with calcium polystyrene sulfonate as well. As such, both sodium and calcium are considered pharmacologically active components of the molecule. This polymetallosulfonate (SPSS or sodium heparin for example) may be further exchanged with any variety of metal cations to prepare mono, di, tri, and even tetravalent metal salt derivatives. Similarly, the polymetallosulfonate, such as SPSS or any sulfated polysaccharide such as heparan sulfate, may be converted to a polyorganosulfonate derivative by exchange of sodium cation for a protonated nitrogen atom containing salt of interest. Additionally, the sulfated polysaccharide may be a proteoglycan with main chain components that include adermatan sulfate, or keratan sulfate, among others. Proteoglycans may include aggrecan, versican or smaller sized species that include decorin, biglycan, fibromodulin, keratocan, osteoglycin, and lumican, among others.

Generally, sulfated saccharides (polysulfonates) are found in their sodium salt forms. However, these compounds may be modified to include nitrogen atom containing salts, among others. In such salts, compounds containing protonatable nitrogen atoms, can include, but are not limited to, amines, amidines, imines, thiazoles, imidazoles, and/or pyridines, among others. Additionally, ammonium salt derivatives may be prepared by the exposure of an amino compound to the acid form of the polysulfonated material, i.e. the sulfonic acid form. In some embodiments, derivatives of material 18 can be produced by chemically or biochemically modifying material 18. In one such example, the cation of material 18 can be modified to include the oligodynamic silver cation ($Ag^+$) by substituting/exchanging $Ag^+$ for sodium ($Na^+$) by the use of a soluble or insoluble silver salt. Examples of silver salts for exchange of silver to material 18 include soluble silver nitrate, or silver acetate which has very low solubility in deionized water or Dowex silver ion modified exchange resins (strong and weak cation exchangers) which have very little if any solubility in deionized water or other aqueous media. Examples of silver ion modified material 18 may include silver polystyrene sulfonate, heparin silver ($Ag^+$), heparan ($Ag^+$) sulfate, or chondroitin ($Ag^+$) sulfate where silver cations are exchanged onto the polysulfated saccharide using a cation resin exchange methodology identical or similar to that described in examples 14 & 15 among others. When polysulfated compounds (material 18) are to be prepared, the type of ion exchange resin that provides good substitution is a weak ion cation exchange resin such as Dowex Mac-3. Silver salts with low deionized water solubility such as silver citrate and the like may be utilized as well. Because of low deionized water solubility, sodium for silver exchange leads to the formation of the exchange product sodium citrate and the consumption of a (molar) equivalent amount of silver citrate to that of the sulfonates present in solution.

Silver has been utilized as an antimicrobial agent especially in the treatment of burns. Although metallic silver develops a surface layer of oxide which tends to passivate the material, in aqueous environments silver ions are readily released and its antimicrobial activity stems from an intracellular accumulation of silver ions. Silver ions readily bind to negatively charged components in proteins and nucleic acids, thereby effecting structural changes in bacterial cell walls, membranes and nucleic acids that affect viability. In particular, it is speculated that silver ions interact with thiol and other groups so that multiple events simultaneously interfere with microbial processes. It is believed that silver ions can bind to DNA to block transcription, bind to cell surface components to interrupt bacterial respiration and interfere with ATP synthesis.

The complex issues concerning the toxicity of silver to mammalian systems have prevented more wide-spread use. Skin discoloration and irritation associated with the use of silver nitrate is well documented; absorption of silver, systemic distribution and excretion in urine has also been reported.

In wound care, silver has been utilized in several products. Silver nitrate is not widely used anymore, but silver sulfadiazine (SSD) and silver releasing dressings have become popular. One unfavorable characteristic of SSD is its low aqueous media solubility thus limiting its penetration through the skin whereas many of the silver salts of polysulfonated material 18 are freely soluble in aqueous media. It is important to note that substitution may be partial or complete. In other words, a metal cation such as silver cation or a molecular cation such as gentamicin may be substituted for sodium or some other relevant cation in varying percentages between 0 and 100%. In one example sodium polystyrene sulfonate (SPSS) may be substituted with silver cation ($Ag^+$) using the method described in example 3 to prepare a mixed sodium-silver polystyrene sulfonate of 14% $Ag^+$ substitution that is completely soluble in deionized water as well as other aqueous media. In another example, a tetracycline as a salt (e.g. hydrochloride) can be substituted for sodium of material 18 via cation exchange. Further, the sulfonic acid derivative of material 18 may be used as a proton source during an acid-base reaction by treatment with, for example, an amino acid such as arginine, or a biogenic amino compound such as tyramine or dopamine. Similarly, the polyanion or polysulfonic acid (anion) of material 18 can be exchanged with a polycation or polyamine, such as a strongly basic ion exchange resin, for example, poly-L-lysine or the poly cationic species polyhexamethylene biguanide.

It is worth noting at this point that just as the cation-exchange modifications to material 18 need not be all (100%), the cross-linking substitutions introduced to alter the solubility of material 18 as described above need not be all (100%) or nothing (0%) and may be engineered to something in between. Instead, some implementations, can specifically utilize partial modifications to achieve useful resultant or derivative materials. In fact, partial cross-linking substitution leaves available sulfonate groups for cation binding and can produce derivative materials that have characteristics that are different from those of the unmodified material 18 and any of the fully substituted derivative materials. For instance with the cation-exchange modified silver analogs described above, where $Ag^+$ for $Na^+$ substitution is carried out, a substitution of less than 100% can result in a material that retains good water solubility and has lower toxicity than the fully substituted counterpart. In one such example, about 14% $Ag^+$ substitution (i.e., ~14 out of every 100 $Na^+$ are substituted by $Ag^+$) can be utilized. In another example, about 34% $Ag^+$ substitution can be utilized. In a further example, about 79% $Ag^+$ substitution can be utilized. The amount of substitution can affect several properties of interest of the derivative material. For instance, the amount of substitution can affect the water solubility of the derivative material. In application where water solubility of the derivative material is desired, a relatively lower percentage of $Ag^+$ for $Na^+$ substitution can be utilized while still offering the beneficial antibacterial properties of silver cation with complete water solubility. For example, the listed 14% and 34% substituted derivative materials are water-soluble yet offer antimicrobial properties against *Staphylococcus aureus, Acinetobacter baumannii*, and/or *Pseudomonas aeruginosa*, among others, for human patients. Similarly, a relatively higher percentage of $Ag^+$ for $Na^+$ substitution, such as the listed 79% example, can be utilized where lower solubility is desired. When Material 18, for example sodium polystyrene sulfonate (SPSS, Material 18-sod) is 100% substituted/exchanged with a cation that does not prevent its dissolution into deionized water, for example with the antibiotic mafenide (Material 18-maf), the derivatized material, Material 18-maf, may be combined with an equimolar amount of Material 18-sod in DI water in order to yield Material 18-maf/sod, where mafenide cations and sodium cations each occupy approximately equal numbers of sulfonate group sites in the polymer. Such a mixed complex can be isolated by lyophilizing the solution to yield a solid mixed salt material 18. This approach works well for repeatedly achieving substitutions where some amount less than 100% are desired and the materials are soluble in water. This methodology makes it relatively straightforward to synthesize a sulfonated material 18 with multiple substitutions at calculated and defined target levels as long as the starting materials are soluble in water and characterizable in terms of their individual substitutions. As such, substitutions where at least two metal cations are included can be prepared at any ratio desired. The same applies to organic cation substitutions and mixed organic-metal cation substitutions as well.

It is also worth noting that while specific substitutions are described in isolation, it is recognized that two or more partial substitutions can be combined to produce derivative materials that have potentially advantageous properties. For instance, partial $Ag^+$ for $Na^+$ substitution can be advantageous for at least two reasons: 1. Silver cation is cytotoxic and the higher the concentration of silver cation the greater the toxicity of the salt to living systems, and 2. As the substitution of silver is increased, the water solubility of the salt generally decreases. Because silver-based antibacterials are generally slow to kill bacterial pathogens, lower water solubility may decrease the effectiveness of such an agent. Although the incorporation of silver cation at 100% of theoretical substitution (for example of $Ag^+$ for $Na^+$) may be a very potent antimicrobial agent, it will be more toxic to fibroblasts, keratinocytes, and other cells than a formulation with a lower level of substitution. For example, Polystyrene sulfonate-Na/Ag (mixed sodium cation/silver cation) at various levels of silver cation substitution (14, 34, and 78 mol %) have been shown to be effective at killing a variety of bacterial organisms. the higher the level of silver substitution, the lower the concentration of Material 18 that is required to kill bacterial pathogens. Material 18 is effective in the micromolar range for 14% Ag substitution, in the nanomolar range for 34% substitution, and in the subnanomolar range for 78% substitution. However, as the silver cation substitution increases the cytotoxicity to neonatal fibroblasts was observed to increase as well.

In other embodiments, Material 18 can be formulated as a salt with three or more cations. For example, material 18 may include partial antibiotic incorporation (such as mafenide), partial for $Na^+$ substitution, and partial $Ag^+$ substitution to produce a material that has a combination of $Ag^+$, $Na^+$, and mafenide cation incorporated. It is also possible to achieve this combination (cation) salt by combining appropriate amounts of a sodium salt of material 18, a mafenide salt of material 18, and a 100% silver salt or mixed sodium-silver salt of material 18, dissolving all three into DI water to achieve a solution and subsequently lyophilizing the solution to a solid. In solution, the salts which are all substituted at 100% of their respective cations, exchange cations rapidly reaching a mixed cation polysulfonated material.

To summarize, material 18 can be associated with numerous elemental cations and cations of compounds that have pharmacologically therapeutic value, either singularly (100% of one cation type) or in combination (two or more cations to make 100%). For example, material 18 can be associated with paramagnetic ions such as $Mn^{+2}$; $Gd^{+2}$, $Fe^{+3}$, as well as radio-opaque metal ions of barium, tungsten, and radioactive ions of strontium, rhenium, yttrium, divalent metal cations $Ca^{+2}$, $Zn^{+2}$, $Cu^{+2}$, $Mg^{+2}$, $Co^{+2}$, monovalent metal cations $Na^+$, $Ag^+$; $Au^+$, $Li^+$, $K^+$, as well as a wide variety of organic cations that includes various antibiotics, among others. Generally, silver cation is antibacterial and exchange onto the polysulfonate yields material 18 with antibacterial properties. Surprisingly, partial silver substitution produces a material 18 that possesses good antibacterial properties, minimal toxicity, and excellent solubility. Example 3 describes the preparation of a partially substituted SPSS-Ag salt (mixed sodium-silver substitution) with excellent solubility. Example 11 describes the materials antimicrobial effectiveness against a variety of bacterial pathogens and example 12 provides an indication of the in vivo effectiveness of a salve formulation containing the partially silver substituted material 18. The preservation of tissue was shown to be statistically better than the control treatment without overt toxicity.

Figure 2:
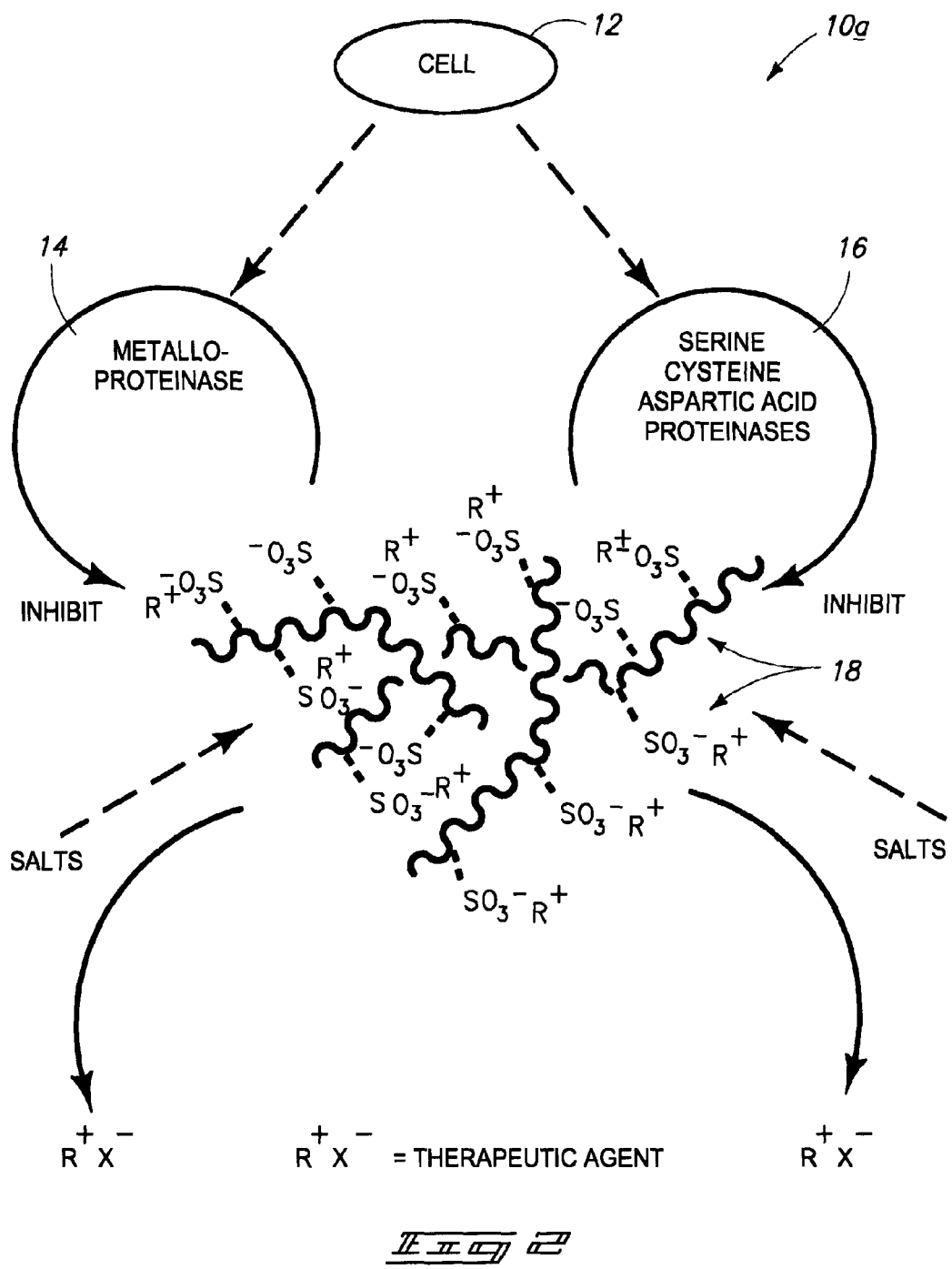
FIG. 2 is an example depicting the interaction of compositions of the disclosure with tissue fluids including salts, and enzymes produced by neutrophils and other cells, according to an embodiment of the disclosure.

Referring to FIG. 2, scheme 10A is shown with material 18 being associated with at least a portion of therapeutic agent R. Example agents $R^+$ associated and/or coupled to material 18 are provided herein. When provided to inhibit inflammation or cancerous cell growth, the portion of therapeutic agent $R^+$ can be released from material 18 and form therapeutic agent $R^+X^-$, via ionic exchange, for example. According to an implementation, material 18 can simultaneously provide proteinase inhibition in addition to a treatment related to therapeutic agent $R^+X^-$. In some cases, the proteinase inhibition capability and the action provided by an ionically bound therapeutic agent can be provided simultaneously.

Figure 3:
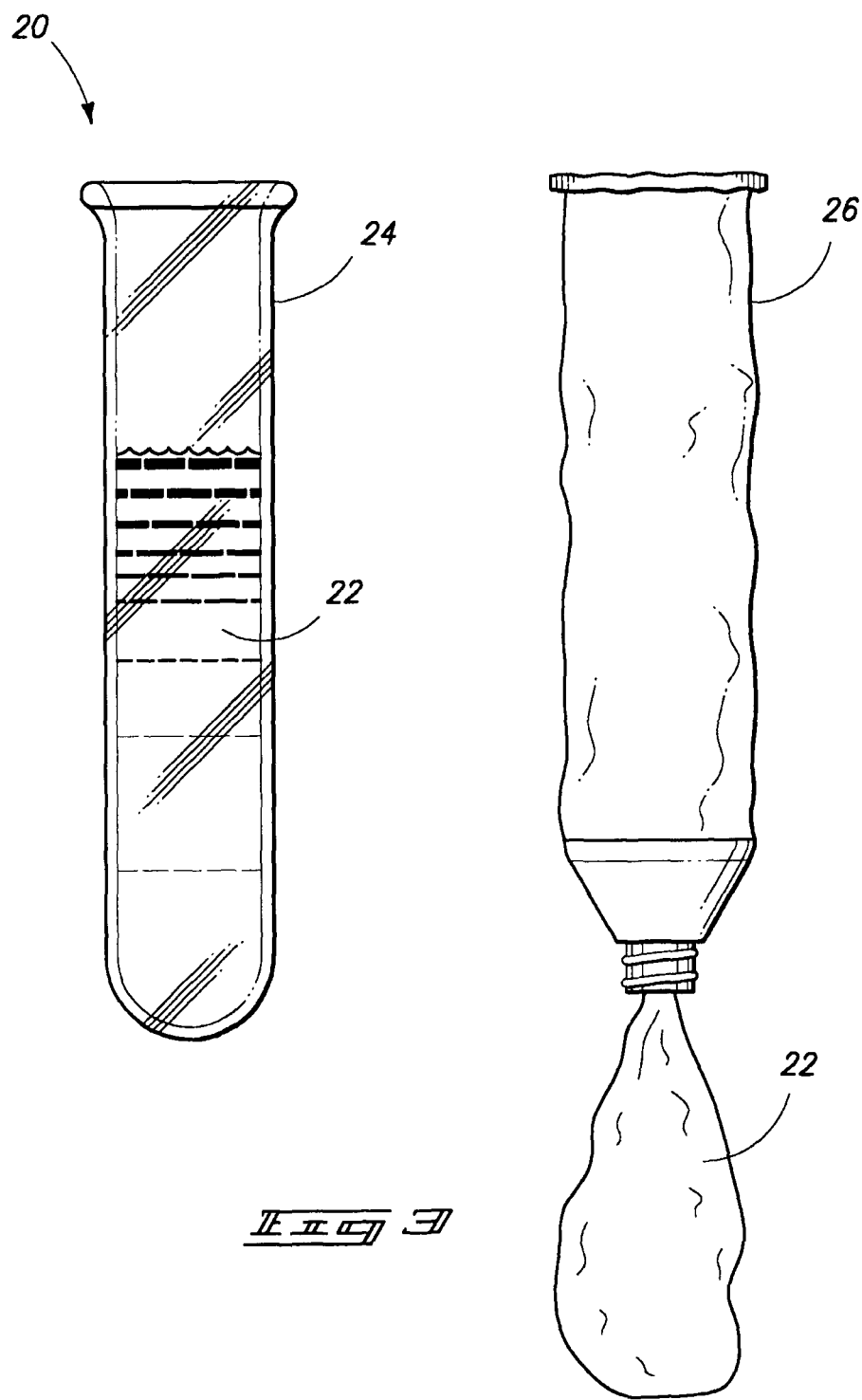
FIG. 3 shows example preparations of compositions of the disclosure according to an embodiment of the disclosure.
Figure 4:
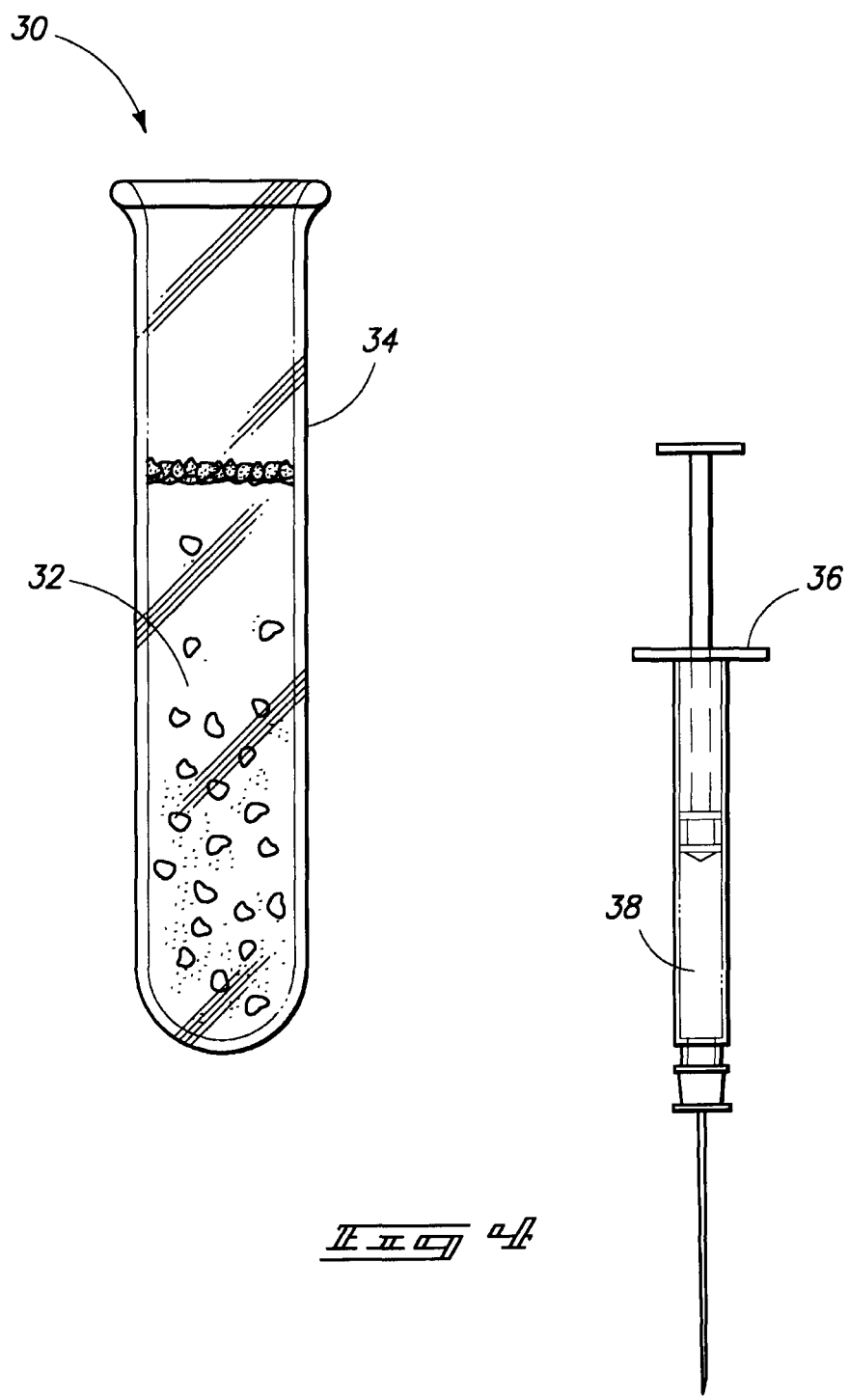
FIG. 4 shows example preparations of compositions of the disclosure according to an embodiment of the disclosure.

Referring to FIGS. 3 and 4, preparations of material 18 are shown in both liquid (FIG. 3) and solid (FIG. 4) form. Referring to FIG. 3, preparation 20 includes a mixture 22 within container 24. Mixture 22 may include at least two components with at least one of the two components being material 18 including a cross-linked form of the polysulfonated material. According to an embodiment of the disclosure, mixture 22 can be a liquid mixture. Material 18 can be present in mixture 22 in the form of a soluble component, for example, or in the form of an insoluble component, as another example. Mixture 22 can include a hydrophilic solvent, such as water, or a hydrophobic component such as petrolatum along with material 18. In one implementation, material 18 can be formulated to be insoluble in deionized water, but soluble in ionic solutions with solubility mediated by the ionic strength. Thus dissolution of the salt and subsequent release of each of the two or more species present in the salt can be modulated by the ionic concentrations, for example, found in biological fluids. Such a occurrence can allow material 18 to be prepared as an insoluble salt in deionized water where two aqueous solutions (for example one of sodium polystyrene sulfonate (SPSS) and one of doxycycline hydrochloride) are combined to yield a deionized water-insoluble polystyrene sulfonate salt of doxycycline (PSS-Dox) which forms as a precipitate that settles out following the combination of the two deionized water solutions. Material 18, in some cases, can be obtained in a relatively pure form by simple filtration. The deionized water-insoluble salt can be slowly dissolved into an isotonic aqueous saline solution, or biologically equivalent solution with sodium, potassium, and/or calcium ions where these ions can exchange with doxycycline ions in order to yield SPSS (or the calcium or potassium salt of PSS) and doxycycline hydrochloride. As used herein, aqueous solutions containing sodium, potassium, and/or calcium ions (simple and relevant biologically relevant salts), as well as amino acids, proteins, peptides or the like are referred to as "aqueous media". Such solutions may include but are not limited to phosphate buffered saline solution (PBS), saline, serum (including fetal bovine serum and human serum), and other biological media. Thus, these deionized water salts can be effective "controlled-release" compounds when placed into or onto biological systems where biological fluids provide the exchange medium for dissolution. Thus, the deionized water-insoluble salts are, in fact, water soluble as long as ions are present and the timescale of dissolution is driven by the cation concentration and the rate of cation exchange. In one example, this form can be administered to a patient directly as a micronized powder that can be placed directly into the periodontal pocket for the treatment of periodontitis, for example. Similarly, the polystyrene sulfonate salt formed by the reaction of sodium polystyrene sulfonate (SPSS) with chlorhexidine digluconate is insoluble in water. Salts that are insoluble in deionized water can interact with the patient's bodily fluids which facilitate the slow dissolution (and subsequent ionization) of material 18 by cation exchange thus leading to protease inhibition and bacterial organism control, for example. In other cases, material 18 can remain completely water-soluble even when 100% exchange of the replacement cation is carried out. For example, a combination of sodium polystyrene sulfonate (SPSS) and mafenide acetate (4-(aminomethyl)benzenesulfonamide acetate salt) in a 1:1 molar combination results in a clear solution that when lyophilized yields a white powder mixture consisting of mafenide polystyrene sulfonate and sodium acetate. The sodium acetate may be dialyzed away using cutoff filters or using dialysis tubing. Other examples of water-soluble salts include those of arginine, carnosine, glutathione, $Ca^{++}$, $Ag^{++}$, and $Co^{++}$. Mixture 22 can also be hydrophobic, such as would be obtained by emulsifying material 18 into a hydrocarbon base along with appropriate additional constituents. Material 18 can be synthesized to be hydrophobic or hydrophilic depending on the choice of cation.

Mixture 22 can include additional components as well as material 18. The additional components may include but are not limited to detergents, emulsifying agents, emollients, antioxidants, excipients, wetting agents, essential oils, flavoring, preservatives, viscosity modifiers, lubricants, petrolatum products, and a skin permeation enhancer. Detergents can include Tween 80 (Polysorbate 80), for example. The skin permeation enhancers can include one or more of a linoleic acid, an alpha-linoleic acid, an oleic acid, cod liver oil, menthol derivatives, squalene, glycerol derivatives, herbal ingredients, and senkyu ether extract. Mixture 22 can be a neutral, hydrophilic matrix cream, lotion, ointment, solution, or gel, and material 18 can be solubilized or dispersed into this mixture. Collectively these kinds of formulations may be referred to as a salve. The gel, for example, can include any variety of largely aqueous based amorphous hydrogel formulations that include, but are not limited to, a hydrophilic water-soluble polymer such as carboxymethylcellulose (CMC), or material 18 can be combined into an ointment which may be a more complex mixture including emulsified formulations. Such an emulsified formulation can include White Petrolatum, Fatty Alcohol (stearyl), Emollient (isopropyl myristate), Emulsifying Agent (polyoxy (40) stearate, sorbitan monooleate), Humectant (propylene glycol), and sterile DI water.

In accordance with an example implementation, mixture 22 can include water and material 18, with material 18 being a polysulfonated salt. Mixture 22 may be buffered to a pH of from about 3.5 to about 8.0 as required to keep the sulfonate groups of material 18 in the desired state. In accordance with another example implementation, mixture 22 can be homogeneous or heterogeneous. For example, mixture 22 can be a homogeneous mixture of water, water-soluble additives, and water-soluble polysulfonated material, as for example in a mouthwash or homogeneous wound gel that may comprise carboxymethyl cellulose for example. As another example, mixture 22 can be a heterogeneous mixture, such as an emulsion, similar to that found in a wound gel or toothpaste. In one such implementation mixture 22 can be in the form of a gel, cream, paste, or lotion, for example. The paste may also include that of a tooth paste for example.

Material 18 may be associated and/or provided with any variety of pharmacologically active cations that can include chemotherapeutic agents for the treatment of a variety of symptoms including: methotrexate; fluorouracil; adriamycin; ansamitocin; cytosine arabinoside; arabinosyl adenine; mercaptopolylysine; PAM; L-PAM (phenylalanine mustard); mercaptopurine; mitotane; procarbazine dactinomycin (actinomycin D); mitomycin; plicamycin (mithramycin); aminoglutethimide; estramustine; flutamide; leuprolide; megestrol; tamoxifen; amsacrine (m-AMSA); asparaginase (L-asparaginase) Erwina asparaginase); etoposide (VP-16); interferon .alpha.-2a; interferon .alpha.-2b; teniposide (VM-26); adriamycin; arabinosyl; procarbazine; and dacarbazine. In accordance with additional embodiments of the disclosure, material 18 may also associated with and/or provided in a preparation with Nitrogen mustards: (Chlorambucil, Chlormethine, Cyclophosphamide, Ifosfamide, Melphalan). Nitrosoureas: (Carmustine, Fotemustine, Lomustine, Streptozocin). Platinum: (Carboplatin, Cisplatin, Oxaliplatin, BBR3464). Busulfan, Dacarbazine, Mechlorethamine, Procarbazine, Temozolomide, ThioTEPA, Uramustine; Antimetabolites: Folic acid: (Methotrexate, Pemeterxed, Raltitrexed). Purine: (Cladribine, Clofarabine, Fludarabine, Mercaptopurine, Thioguanine). Pyrimidine: (Capecitabine). Cytarabine, Fluorouracil, Gemcitabine; Vincaalkaloids: (Vinblastine, Vincristine, Vindesine, Vinorelbine); Cytotoxic/antitumor antibiotics: Anthracycline family: (Daunorubicin, Doxorubicin, Epirubicin, Idarubicin, Mitoxantrone, Valrubicin). Bleomycin, Mitomycin; Topoisomerase inhibitors: Topotecan, Irinotecan; Monoclonal antibodies: Alemtuzumab, Bevacizumab, Cetuximab, Gemtuzumab, Panitumumab, Rituximab, Infliximab, Tositumomab, Trastuzumab, Etanercept; Photosensitizers: Aminolevulinic acid, Methyl aminolevulinate, Porfimer sodium, Verteporfin; Kinase Inhibitors: Dasatinib, Erlotinib, Gefitinib, Imatinib, Lapatinib, Nilotinib, Sorafenib, Sunitinib, Vandetanib (ZD6474).

Additional compounds that may be provided and/or associated with material 18, include: Altretamine, Anagrelide, Bortezomib, Denileukin diftitox, Estramustine, Pentostatin, Pegaspargase, Alagebrium (3-phenacyl-4,5-dimethylthiazolium, anti-helmintics; antitoxins; antivenins; aminoglycosides; theophylline; aminophylline; hemin; hematoporphyrins; muramyldipeptide; muramyltripeptide; lymphokines; macrophage activation factor; N-acetyl-muramyl-L-alanyl-D-isoglutamine; ketoconazole; nystatin; griseofulvin; flucytosine (5-fc); miconazole; amphotericin B; ricin; cyclosporins; sulfazecin; growth hormone, melanocyte stimulating hormone; triamcinolone; fludrocortisone; oxytocin; vassopressin; cyanocobalamin; super oxide dismutase; alkaline phosphatase; amelexanox; glutathione; carnosine; p-aminosalicylic acid; isoniazid; capreomycin; cycloserine; ethambutol; ethionamide; pyrazinamide; rifampin; and streptomycin; acyclovir; amantadine azidothymidine; ribavirin and vidarabine; diltiazem; nifedipine; verapamil; dapsone; octenidine; chloramphenicol; neomycin; cefaclor; cefadroxil; cephalexin; erythromycin; clindamycin; lincomycin; bacampicillin; carbenicillin; dicloxacillin; cyclacillin; picloxacillin; hetacillin; methicillin; nafcillin; oxacillin; penicillins (G&V); ticarcillin; rifampin; doxycycline; minocycline, mefenamic acid; oxyphenbutazone; phenylbutazone; piroxicam; sulindac; tolmetin; chloroquine; hydroxychloroquine; metronidazole; quinine; quinidine; meglumine; penicillamine; paregoric; codeine; heroin; methadone; morphine; opium; and papaverine; noscapine; deslanoside; atracurium; gallamine; metocurine; pancuronium; succinylcholine (suxamethonium); tubocurarine; vecuronium; ethchlorvynol; flurazepam; glutethimide; methotrimeprazine; methyprylon; midazolam; temazepam; triazolam; bupivacaine; chloroprocaine; etidocaine; lidocaine; mepivacaine; procaine; marcaine; tetracaine; droperidol; etomidate; fentanyl; ketamine; benzyl trimethyl ammonium; chlorhexidine; amino acids (natural & synthetic); nicotinic acid; nicotinamide, pyridoxine; nucleosides (purines); thiamine; coenzyme A; pentoxifylline; 3-amino-4-hydroxybutyric acid; 6-diazo-5-oxo-L-norleucine; aceclofenac; acediasulfone; alminoprofen; amfenac; amoxicillin; ampicillin; apalcillin; apicycline; aspoxicillin; azaserine; aztreonam; bambermycin(s); biapenem; bromfenac; bucillamine; bumadizon; candicidin(s); carbenicillin; carprofen; carumonam; carzinophillin A; cefamandole; cefatrizine; cefbuperazone; cefclidin; cefdinir; cefditoren; cefepime; cefetamet; cefixime; cefinenoxime; cefminox; cefodizime; cefonicid; cefoperazone; ceforanide; cefotaxime; cefotetan; cefotiam; cefozopran; cefpimizole; cefpiramide; cefpirome; cefprozil; cefroxadine; ceftazidime; cefteram; ceftibuten; ceftriaxone; cefuzonam; cephaloglycin; cephalosporin C; cephradine; ciprofloxacin; clinafloxacin; cyclacillin; denopterin; diclofenac; edatrexate; enfenamic acid; enoxacin; epicillin; etodolac; flomoxef; flufenamic acid; grepafloxacin; hetacillin; imipenem; lomefloxacin; lymecycline; meclofenamic acid; melphalan; meropenem; moxalactam; mupirocin; mycophenolic acid; nadifloxacin; niflumic acid; norfloxacin; oxaceprol; panipenem; pazufloxacin; penicillin N; pipemidic acid; podophyllinic acid 2-ethylhydrazide; procodazole; pseudoephedrine; pteropterin; quinacillin; ritipenem; romurtide; S-adenosylmethionine; salazosulfadimidine; sparfloxacin; streptonigrin; succisulfone; sulfachrysoidine; sulfaloxic acid; teicoplanin; temafloxacin; temocillin; tetracycline; tolfenamic acid; (N-((5-(((1;4-Dihydro-2-methyl-4-oxo-6-quinazolinyl)methyl)methylamino)-2-thienyl)carbonyl)-L-glutamic acid); tosufloxacin; trovafloxacin; doxyxycline; mafenide; minicycline; tigemonam; or vancomycin; lucensomycin; natamycin or; 6-diazo-5-oxo-L-norleucine; denopterin; edatrexate; eflomithine; (N-((5-(((1;4-Dihydro-2-methyl-4-oxo-6-quinazolinyl)methyl)methylamino)-2-thienyl)carbonyl)-L-glutamic acid)-ubenimex. In accordance with yet another example, material 18 can be associated and/or provided with albuterol, terbutaline, and/or ephedrines, as well as natural or synthetic peptides.

Mixture 22 can be provided to an application apparatus such as application apparatus 26. In the depicted embodiment, apparatus 26 is a collapsible tube. Mixture 22 can take the form of a lotion or gel which can be extruded from apparatus 26 upon application of force. In accordance with another embodiment, mixture 22 can be provided to a container configured for pressurization such as an aerosol can or an inhaler. In one implementation, mixture 22 can include a propellant and material 18. Under pressure in a confined container, mixture 22 can be expelled from the pressurized container in aerosol form. Mixture 22 may be provided from a nebulizer or inhaler as well.

Referring to FIG. 4, preparation 30 is shown that includes particles 32 within container 34. Particles 32 can be solid and include polysulfonated material 18, for example. In accordance with an example configuration, individual ones of particles 32 can be hydrogel beads. The hydrogel of the hydrogel beads can be manipulated to include material 18. For instance, the hydrogel can be cross-linked in the presence of, and/or blended with, material 18 to form a solid blend. The hydrogel can polyethylene glycol-based and/or polyvinyl alcohol-based, for example. In accordance with other embodiments of the disclosure, material 18 can be dispersed into a solid matrix of cross-linked acrylic acid-based polymer such as methacrylic acid or any of its esters including poly (2-hydroxy ethyl methacrylate) (HEMA), polypropylene oxide, polyethylene oxide, polyvinyl alcohol, a polyurethane, a polyester, alginate, silicone, hydrocolloid, and/or other hydrogels, or an alkylene polymer (polyalkylene) such as polypropylene or polyethylene. Further, individual ones of particles 32 can include poly(N-vinyl pyrrolidone), poly(vinyl alcohol), poly(acrylic acid), polyacrylamide including poly(N-isopropylacrylamide), poly(ethylene-co-vinyl acetate), poly(ethylene glycol)/polyethylene oxide, poly (methacrylic acid), polyurethanes, and silicones, among others.

In accordance with another implementation, individual ones of particles 32 can include material 18 as a biodegradable polymer or material 18 associated with a biodegradable polymer. Example biodegradable polymers include, but are not limited to, lactide/glycolides, polyglycolides, polyorthoesters, and/or polylactides, polycaprolactones, polydioxanones, starches, cellulose, chitosan, and cross-linked natural polymers such as collagen, gelatin or elastin.

In some implementations, individual ones of the particles can be microspheres that include material 18. In accordance with another implementation, individual ones of particles 32 can include a degradable substrate, such as collagen, for example. Individual ones of particles 32 can also include gelatin or the heterosaccharide pectin.

Individual ones of the particles 32 can be microspheres that include material 18. In accordance with another implementation, individual ones of particles 32 can include a degradable substrate, such as collagen, for example. Individual ones of particles 32 can also include gelatin or the heterosaccharide pectin.

As an example, apparatus 36 can be used to apply particles 32. An example of apparatus 36 includes a syringe; however additional applicators may be utilized, such as gauze and/or collapsible tubing. In accordance with an example embodiment, particles 32 may be provided to apparatus 36 in the form of an injectable mixture. Particles 32 within the injectable mixture may or may not be dissolved once injected. In accordance with another implementation, particles 32 can be material 18 of mixture 22. As a component of mixture 22, particles 32 may be provided as material 18 according to example embodiments.

Referring to FIGS. 3 and 4, preparations 20 and 30, respectively are not mutually exclusive. Compositions that may be included within mixture 22 may also be incorporated into particles 32. Likewise, compositions that may be included within particles 32 may also be incorporated into mixture 22. According to example implementations, preparations 20 and/or 30 may include biologically active material. Example biologically active materials can include, but are not limited to, one or more of peptides, proteins, cytokines, healing factors, antibiotics, cytotoxins, VEGF, PDGF, EGF or other relevant growth factors, including, but not limited to exogenous growth factors. Preparations 20 and/or 30 may also include one or more of an angiogenesis stimulant, antibacterial, antibiotic agent, or antiangiogenic agent. According to an example implementation, material 18 may inhibit the degradation of exogenous and/or endogenous factors. For example, material 18 may be provided along with an exogenous material of an organism. Material 18 may prevent the degradation of the exogenous material providing for the retained therapeutic activity of the exogenous material. Material 18 and the exogenous and/or endogenous materials may be provided simultaneously to the organism.

Material 18 may also be associated with a solid and fabricated into the form of a sheet or a coating. For example, Material 18 may be prepared to have antimicrobial properties and may be fashioned into a solid formulation for the treatment of burns or infected wounds as with a dressing, as inclusion into a coating for medical device or into a solid sheet protective component around a device where a breach in the skin may increase the likelihood of infection. As a component of a wound dressing, material 18 may be associated with, but not limited to, natural biopolymers such collagen, gelatin, or biomedical materials that include polyurethanes, silicones, and hydrogels for example.

Preparations 20 and/or 30 may have a concentration of material 18 of about 1 mg/ml, although higher or lower concentrations can be used if desired. For example, concentrations as low as about 0.01 µg/ml, or as high as the limit of solubility of material 18 in mixture 22 and/or particles 32, may be used in a formulation such as amorphous gel or solid dressing such as a those fabricated of calcium alginate or a hydrogel. Preparations 20 and/or 30 may contain a concentration of material 18 of from about 0.00001 to about 500 mg/ml depending upon the toxicity of the material to the living organism.

Preparations 20 and/or 30 may be applied via short or long term application. Preparations including vehicles such as sterile phosphate buffered saline (PBS) or sterile deionized water are suitable for short term application of material 18. For longer term application, use of a slow release vehicle may be utilized. For example, a gel formulation preparation can be used for effective delivery of material 18.

Figure 5:
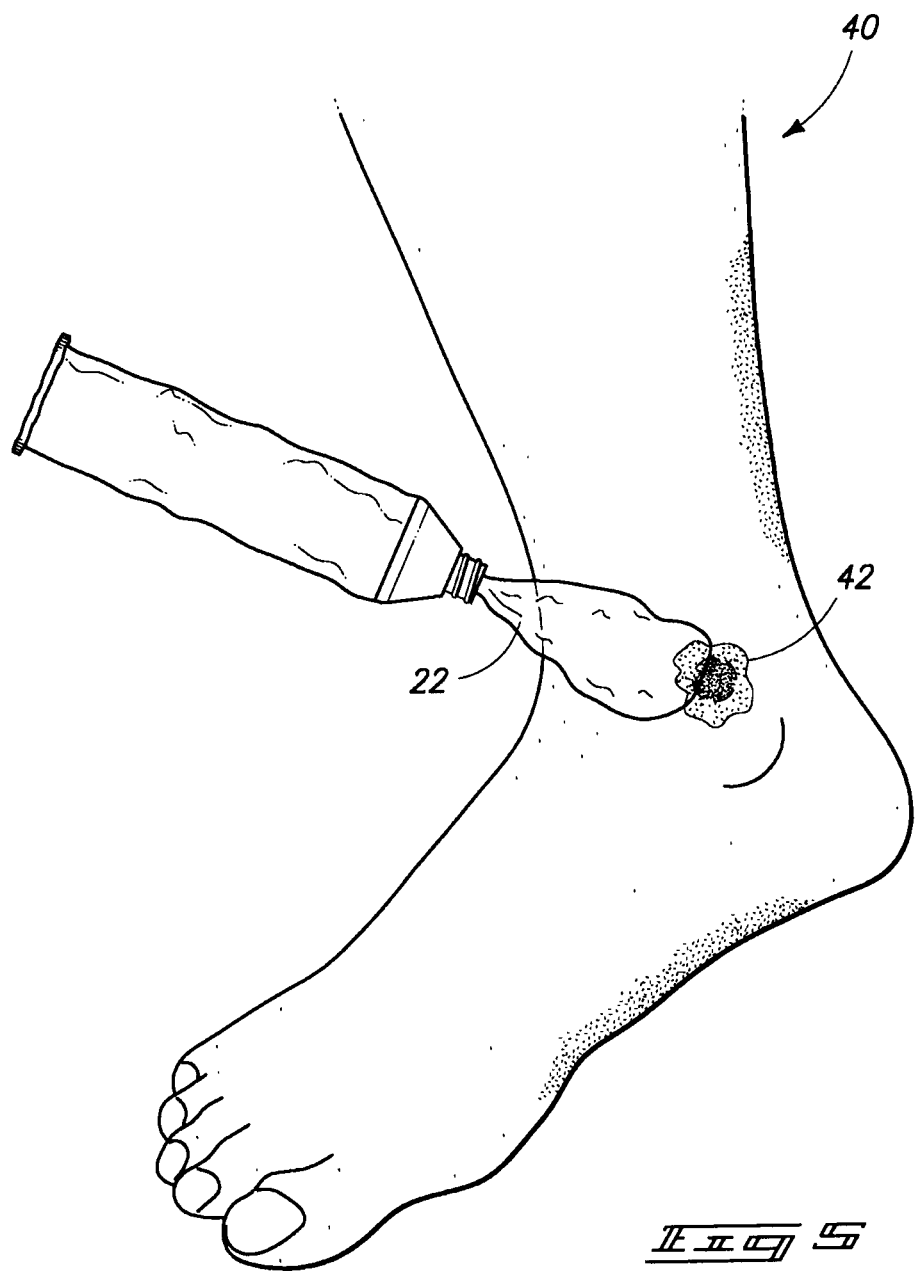
FIG. 5 is a depiction of an example application according to an embodiment of the disclosure.

Referring to FIGS. 5 and 6, example methods for applying preparations 20 and 30 are depicted. In accordance with example embodiments, these methods can promote the healing of tissue of a multicellular organism, including but not limited to vertebrate organisms. In accordance with example implementations, a therapeutically effective amount of material 18 can be administered to the organism to reduce one or both of inflammation and cancerous cell growth.

In other embodiments, a porous collagen substrate or construct, for example a sponge, or an electrostatically processed (electrospun or electrosprayed) collagen substrate or construct is formulated to include one or more of material 18, a growth factor, an angiogenic agent, a nutrient, a nitric oxide donor or precursor, and optionally mammalian cells. The combination of the biodegradable substrate, for example a collagen or gelatin, and a growth factor along with material 18 provides a basis for dermal and subdermal healing, i.e. a dermal substitute. Material 18 is combined with the growth factor in order to protect the growth factor from degradation that may result as a consequence of the presence of inflammatory cells and hence proteases. Dermal substitutes are born from the idea of re-engineering tissue and its components, i.e. "tissue engineering". In the aforementioned examples a substitute may be cellular or acellular in nature. Acellular substitutes are attractive because they are less costly and handling/manufacturing is simpler as the presence of living cells is restrictive when sterilization and shelf life are concerned. An acellular substitute may have application in the repair of skin, for example, where a cancerous growth has been removed, where a patient has had a prolonged open wound, or where a patient has been severely burned and requires rapid grafting but lacks sufficient tissue to provide a "homograft". Of course a cellularized substitute may also be used, however the cost for such a substitute will be significantly higher.

In electrospinning, polymer solutions, or melts, are deposited as overlapping (continuous) fibers thus creating mats rather than droplets as a consequence of the advantageous entanglement of chains within melts or solutions at sufficiently high polymer concentrations. The fibers are derived by charging a liquid typically to 5-30 kV vs. a ground a short distance away, which leads to charge injection into the liquid from the electrode. The sign of the injected charge depends upon the polarity of the electrode; a negative electrode produces a negatively charged liquid. The charged liquid is attracted to the ground electrode of opposite polarity, forming a so-called Taylor cone at the nozzle tip and, eventually, a fiber jet as the electric field strength exceeds the surface tension of the solution. The continuous fiber is collected at the opposite electrode in a form that can be controlled by the geometry and movement of the ejection electrode and the collecting electrode.

In general, chronic wounds can be characterized by a prolonged inflammatory phase, which ultimately can result in elevated protease activity and the subsequent degradation of growth factors and other positive wound healing factors, with the overall effect being impaired healing. Chronic wounds can be considered an imbalance between tissue deposition, stimulated by growth factors, and tissue destruction mediated by proteases. Chronic wounds of diverse etiologies can have elevated levels of a specific class of proteolytic enzymes known as the matrix metalloproteases (MMPs). The effects of these high levels of MMPs in the wound environment may include local destruction of growth factors and their receptors as well as degradation of granulation tissue components.

While the overall goal of wound healing is to synthesize and deposit new tissue so as to reestablish continuity and function, it can be noted that controlled tissue degradation is a normal part of the wound healing process. Much of the tissue degradation related to wound healing is performed by MMPs. The MMPs are a family of structurally related, protein-degrading enzymes that require calcium ions for structural conformation and zinc ions in their active site for function. About 20 different members of the family have been identified, and they share similar structure (about 40% amino acid homology). Multiple cell types, including macrophages, fibroblasts, neutrophils, epithelial cells, and endothelial cells, synthesize MMPs in the presence of specific biochemical signals, such as inflammatory cytokines (e.g., TNF*, IL-1b). MMPs play a role in many normal physiological processes, such as wound healing, embryonic development, and menstruation. An individual MMP may have one or multiple protein substrates that it degrades. Certain MMPs are very specific in their function (e.g., the collagenases only degrade collagen). Specifically, they cleave the collagen triple helix at a single point. This cleavage then allows the rigid triple helix to relax and unravel, resulting in two gelatin fragments. Other MMPs have multiple substrates; some redundancy of substrates between MMPs is evident. When redundancy exists, usually one MMP degrades a particular substrate preferentially.

Collectively, the MMP family of enzymes is capable of digesting almost all of the components of the extracellular matrix. In order for healing to progress and result in repair, a balance may exist between the protein-degrading activities of MMPs and other cellular activity directed towards the synthesis and deposition of the protein components of granulation tissue. The proteolytic activity of MMPs is controlled by various mechanisms, including gene transcription, production of the enzyme in an inactive form (called a zymogen) that requires extracellular activation, and by local secretion of endogenous enzyme inhibitors called tissue inhibitors of metalloproteases (or TIMPs). The same cells that produce MMPs can synthesize TIMPs. Four different TIMPs have been identified in tissues (TIMP-1, TIMP-2, TIMP-3, and TIMP-4). These TIMPs can inhibit all of the MMPs by binding to the zinc-containing active site of the enzyme. TIMPs do not bind to the zymogen form of the enzyme. During normal wound repair, a delicate balance can exist between the MMP and TIMP activity levels. If the balance is disturbed, high levels of MMPs may result in excessive tissue degradation or destruction of other protein components in the extracellular matrix (ECM), such as growth factors, cell surface receptors, and even the TIMPs themselves.

At least one other characteristic of some chronic wounds is the excess of proteases that are detected in the extracellular space. While controlled degradation can occur during normal wound healing, excess or prolonged proteolytic activity is considered detrimental and thought to contribute to the lag in healing of the wound. In some instances, excess bacterial loading in wounds can postpone healing. Material 18 can be effective at addressing bacterial loading and excessive proteolysis of chronic wounds leading to faster and better healing.

With regard to cancerous cell growth, some of the neutrophil and other cell-induced tumor-promoting effects are attributed to their abilities to express and release proteases. Neutrophil degranulation results in the release of serine proteases, such as elastase, cathepsin G and protease-3, which may contribute to the activation of MMPs that mediate tumor cell invasiveness.

Tumorigenesis involves not only tumor cells that become transformed but also the tumor stroma which reacts by inducing inflammatory and angiogenic responses. Angiogenesis, the formation of new capillaries from preexisting vessels, is typically required for tumor growth and metastasis. During angiogenesis, quiescent endothelial cells are activated and they initiate migration by degrading the basement membranes through the action of specific (expressed) proteins, in particular, MMPs.

MMPs promote tumor progression not only through ECM degradation but also through signaling functions. MMPs counter apoptosis, orchestrate angiogenesis, regulate innate immunity, and promote metastasis and tumor growth. Stromal and immune-defense responses can eventually fail, resulting in immune-cell evasion, phenotypic evolution of metastases, chemotherapeutic resistance and further tumor dissemination. MMP binding to cell-surface proteins may have an effect on intracellular signaling, facilitate proenzyme localization and activation, mediate cell motility by disruption of cell contacts with the ECM, and promote internalization of the enzyme. For example, integrins are shown to act as receptors for several proteases, including MMPs. Such interactions have been detected in caveolae, invadopodia, and at the leading edge of migrating cells, where directed proteolytic activity is likely to be needed. The first interaction between an integrin and an MMP (MMP-2) was identified on the surface of melanoma cells and angiogenic blood vessels. Furthermore, MT1-MMP was shown to activate the integrin, αVβ3, through proteolytic cleavage. Additionally, αVβ3-integrin may have modulatory properties on MMP-2 activity by binding to its C-terminal domain.

Further, CD44, which is the principal receptor for hyaluronan, can also serve as a MMP-9-docking molecule. Interaction of MMPs with the cell surface not only may be needed for proenzyme activation and targeting at specific sites for degradation of cell-surface substrates, but also could promote intracellular degradation via receptor-mediated endocytosis.

Leukocyte elastase (LE) is a serine protease, expressed by polymorphonuclear (PMN) leukocytes, mainly neutrophils. LE acts both at the intra-cellular level to kill engulfed pathogens, and at the extra-cellular level as mediator of coagulation, immune responses, and wound debridement. Since LE has the potential to degrade some structural proteins of the extra-cellular matrix (ECM), such as elastin, fibronectin and collagens, production of excess amounts of active LE has been identified in a number of pathological conditions leading to impairment of ECM organization that include rheumatoid arthritis, emphysema, chronic obstructive pulmonary disease (C.O.P.D.), cystic fibrosis, some chronic wounds, inflammatory bowel diseases, and tumor progression for example. LE also activates the pro-enzymatic form of matrix metalloproteinase-9 (MMP-9) massively released by the PMNs, and instrumental to their extravasation. Human tissues are normally protected from excessive LE activity by endogenous inhibitors such as α1-protease-ihibitor (α1-PI), α2-macroglobulin, and secretory leukoprotease inhibitor (SLPI). An enzyme/inhibitor imbalance may lead to increased lysis of ECM macromolecules and thus an increased risk of tissue injury in areas infiltrated by activated PMNs. Furthermore, given the ability of LE to degrade multiple cytokines, receptors, and complement components, a negative modulation of the inflammatory response may favor antigen persistence, leading to chronic inflammation. As for the possibility of using exogenous LE-inhibitors for therapeutic purposes, to date many of the inhibitors that have been developed present side effects that make them less than ideally suitable for human use. However, material 18 may be provided to the organism in an effort to protect both exogenous and endogenous factors.

Referring to FIG. 5, organism 40 may have a wound 42, such as an epidermal wound. Example wounds include, but are not limited to, burns (thermal and chemical) and chronic ulcers, such as pressure ulcers, diabetic ulcers, venous leg ulcers, and periodontitis. Wound 42 can also include atopic dermatitis, a common form of inflammation of the skin and characterized by elevated tissue levels of cathepsin G. Atopic dermatitis is a chronic skin disorder characterized by pruritus, dry skin, and excoriation, which may be localized to a few patches or involve large portions of the body. Wound 42 can also be surgical or the result of trauma such as abrasions, skin tears, and/or blisters.

In accordance with the embodiment depicted in FIG. 5, mixture 22 including material 18 can be administered topically to wound 42. As described above, mixture 22 can be a liquid such as a gel, cream, or lotion. In accordance with another implementation, mixture 22 including material 18 can be applied to a substrate such as a gauze or sponge, and the substrate can be applied to wound 42.

Upon administration of material 18, protein degradation of the tissue of organism 40 can be inhibited. In accordance with example implementations, protein degradation can be prevented via the inhibition of proteases including metalloproteinases, such as collagenase (MMP-8) and gelatinase (MMP-9) for example. Inhibition of cysteine, aspartic acid, serine proteases and metalloproteinases can also be accomplished. The serine proteases inhibited can include one or both of elastase and cathepsin G. The cysteine proteinases that may be inhibited include cathepsins S & K both of which have isoelectric points in excess of 8.0.

Mixture 22 may be applied to wound 42 daily, or more or less frequently as required. A typical daily dosage of material 18 will be 20 millunits/g/cm$^2$ of the wound or ulcer, although it will be recognized that this amount may be varied, and concentrations of 0.1-2000 mu/g/cm$^2$ advantageously may be used. For example, ulcers of long duration (such as one year or longer) may require concentrations of 500 mu/g/cm$^2$ applied multiple times per day, such as, for example, 2, 3, or 4 times daily. For ulcers of lesser duration, or those that are responding well to higher doses, the dose may be lowered. For example, the protease inhibitor dose may be lowered sequentially to, for example, 100, 10, 1, or 0.1 mu/g/cm$^2$. In addition, the application of the inhibitor may be made less frequently, such as from 4 to 1 times daily.

Referring to FIG. 6, tissue 52 is shown having composition 38 applied thereto. Tissue 52 includes both cancerous cells 56 and non-cancerous cells 54. In accordance with an example embodiment, a therapeutically effective amount of composition 38 including material 18 associated with a solid material, such as a microspheres or bead, can be administered internally to reduce one or both of inflammation and cancerous cell growth.

The solid components or particles comprising material 18, including some of its cross-linked forms, may be formulated into mixture 22 that may be configured as a biodegradable mass such as a microsphere or wafer incorporating an anti-tumor agent. Anti-tumor agents may include but are not limited to angiogenesis inhibitors, DNA intercalators & cross-linkers, DNA synthesis inhibitors, DNA-RNA transcription regulators, enzyme inhibitors, gene regulation compounds, microtubule inhibitors, as well as other agents that address different biological processes or biological process inhibitors. Such a wafer or microspherical particle formulation may be implanted at the site of a tumor for example. In such an example, the controlled degradation of the particles will slowly release the polysulfonated material and its ionically bound therapeutic agents thus addressing proteases and cell growth directly at the site of implantation. The materials that are known to be biodegradable that may be combined with material 18 to form a Mixture 22 include but are not limited to lactide-glycolide copolymers, polyorthoesters, polycaprolactones, polydioxanones, starches, cellulose, chitosan, and cross-linked natural polymers such as collagen or elastin.

Referring to FIG. 7, a solid sheet of biomedical polymer such as a silicone gel is formulated to include a material 18, such as PSS-chlorhexidine and fashioned into a collar 60 that is placed at the base of a cannula 63 as a component of a subcutaneous infusion set 58 or at the entry point of venous access line 65 of a PICC (peripherally inserted central catheter) line both of which can be associated with a drug delivery system. Collectively these are referred to as transcutaneous access devices. These devices are for the delivery of liquid substances into the human body or the removal of, or access to analytes within the human body such with a biosensor. All of these devices possess an entry point herein referred to as a transcutaneous access point. It is understood that the collar 60 may be formulated from a variety of different biomedical polymers in addition to silicone gel and that the collar may be fabricated into a variety of shapes such as that resembling but not limited to a doughnut 61 or a half moon 62 for example and may be applied to any variety of transcutaneous access devices.

Other antimicrobial PSS formulations may also be used such as PSS-doxycycline, PSS-polyhexamethylene biguanide, or PSS-octenidine. Such a system includes insulin delivery systems such as insulin pumps/infusion sets, central venous lines like PICC lines, as well as implanted access ports such as a MediPort or Port-a-Cath. Other antimicrobial formulations that do not include a polysulfonated material 18 may also be incorporated in such a collar 60 as described. For example, chlorhexidine diacetate or other antimicrobial agent alone or in combination can be incorporated into a collar 60 as described. Furthermore, it is understood that other healing aids may be added to the collar. Examples of healing aids include but are not limited to antioxidants, vitamins, growth factors, peptides, amino acids, and cytokines.

It is understood that such a system may have additional benefits beyond preventing infection. The benefit includes providing a protease inhibitor to a site where the open wound may facilitate degradation of the protein drug for example. Degradation of a protein drug as a consequence of inflammation and consequential proteolytic activity in the (subcutaneous wound) space where the drug is delivered may reduce the effective dose of the therapeutic compound, and in addition the fragments of the protein that result from proteolytic degradation of the drug can be proinflammatory components thus leading to an exacerbated inflammatory response at the site of delivery. This continuous inflammation can lead to the inability of the subcutaneous space, where the drug cannula 60 resides, to effectively absorb the drug.

Example embodiments of the disclosure are provided below.

EXAMPLE 1

Preparation of Material 18 (PSS-Arginine)

Sodium Polystyrene Sulfonate (SPSS, 70,000 mw) acquired from Sigma-Aldrich, PO Box 14508, St. Louis, Mo.

63178, UNITED STATES and purified by precipitation from a 20-25% solution in deionized water into isopropanol, can be dissolved into deionized water to yield a 10-25% solids solution. Separately, arginine base in deionized water (10 mg/mL) is added to account for an equimolar quantity of sodium polystyrene sulfonate (SPSS), and the solution stirred for 1 hour at room temperature. The solution is transferred into a lyophilizer container and frozen. The frozen mass is placed under vacuum of the lyophilizer and the solid polystyrene arginine sulfonate is isolated as a flocculent off-white solid.

EXAMPLE 2

Preparation of Material 18 (PSS-Mafenide)

Sodium Polystyrene Sulfonate (SPSS, 70,000 mw) acquired from Sigma-Aldrich, PO Box 14508, St. Louis, Mo. 63178, UNITED STATES and purified as described in Example 1 can be dissolved into deionized water to yield a 10-25% solids solution. Separately, 4-Aminomethylbenzenesulfonamide acetate is dissolved into deionized water (10 mg/mL) and is added to account for an equimolar quantity of sodium polystyrene sulfonate (SPSS), and the solution stirred for 1 hour at room temperature. The solution is transferred into a lyophilizer container and frozen. The frozen mass is placed under vacuum of the lyophilizer and the solid polystyrene mafenide sulfonate is isolated as a flocculent off-white solid.

EXAMPLE 3

Preparation of Material 18 (PSS-Ag)

Sodium Polystyrene Sulfonate (SPSS, 70,000 mw) acquired from Sigma-Aldrich, PO Box 14508, St. Louis, Mo. 63178, UNITED STATES and purified as described in Example 1 can be dissolved into deionized water to yield a 10-20% solids solution. Separately, silver acetate (Fluka) can be suspended into deionized water, stirred, and the mixture heated to 60° C. while maintaining stirring. To the stirring mixture, 100 g of Dowex® Marathon strong cation exchange resin (Dow Chemical) can be added to the mixture and dissolution/disappearance of the silver acetate immediately follows. The $Ag^+$ modified Dowex® Marathon strong cation exchange resin, which is in fact a water-insoluble salt, can be isolated, washed with deionized water and dried. The $Ag^+$ modified cation-exchange resin is photo sensitive and should be stored away from room light. The dried, $Ag^+$ modified Dowex® Marathon strong cation exchange resin is added to the 10-20% solution of sodium polystyrene sulfonate (SPSS) in a jar with a PTFE lined cap, the jar is sealed and placed onto a roller mill for about one hour. Subsequently, the Dowex® resin is filtered from the solution, washed with deionized water and the resulting solution placed into a lyophilizer vessel, the solution is frozen, and the lyophilizer vessel containing the frozen material is connected onto the lyophilizer until only a powder remains. The percentage of silver incorporation onto the PSS backbone is dependent upon the relative excess of silver-modified Dowex® resin utilized. Adjustment (lowering) of the ratio of silver to sodium in the silver-modified PSS can be accomplished by blending solutions of sodium polystyrene sulfonate (SPSS) and PSS-Ag (with Ag substitution up to 100%) and lyophilizing the equilibrated solution. Note: A 20% substituted PSS-Ag as determined by atomic absorption (20% Ag, 80% Na) can be combined with an equimolar amount of SPSS in solution and the solution lyophilized to yield a 10% Ag substituted PSS.

EXAMPLE 4

Preparation of Material 18 (Tecophilic Polyurethane Film Containing Sodium Polystyrene Sulfonate)

Sodium Polystyrene Sulfonate, 5 grams, (SPSS, 70,000 mw) acquired from Sigma-Aldrich, PO Box 14508, St. Louis, Mo. 63178, UNITED STATES and purified as described in Example 1 can be combined with 45 g of hydrophilic polyurethane (SPSS formulation) and the mixture dissolved into a 95:5 mixture of ethanol-deionized water to yield a 10% solids solution. The solution can be cast in to a film, air dried and vacuum dried to yield a flexible material. The polymer-SPSS formulation can be used to evaluate the effect of SPSS against elastase. The results are detailed in FIG. 8. Note that the SPSS formulation (1) has reduced the elastase from 30 milliunits to approximately 6 milliunits reflecting a roughly 80% decrease in activity as depicted in the example.

EXAMPLE 5

Preparation of Material 18 (Amorphous Hydrogel Gel Containing Sodium Polystyrene Sulfonate About 15 g of Cutinova amorphous hydrogel (Beiersdorf AG, Unnastraβe 48, D-20245, Hamburg, Germany) can be transferred to a vial and 1.67 g of sodium polystyrene sulfonate (SPSS) (mw=70,000) (Sigma-Aldrich, PO Box 14508, St. Louis, Mo. 63178, UNITED STATES) added and the SPSS stirred into the gel using a glass rod to yield about a 10% (wt./wt.) solids composition (188-DJV). The data are presented for the SPSS formulation in the Cutinova gel (188-DJV). The bar graph (FIG. 9) reveals that nearly 80% of the serine protease elastase is removed from the test sample (human wound fluid).

EXAMPLE 6

Application of Material 18

The elastase inhibiting capacity of the sample from example 5 above (DJV-188) can be compared against Sodium Polystyrene Sulfonates (SPSS 70K and 1000K) dissolved in buffer. These identifiers are molecular weights of these materials. These SPSS-containing formulations can also be compared to Cutinova gel (same as unlabeled gel), a water-insoluble strong cation-exchange polymer (nuggets), the 70K and 1000K molecular weights of SPSS, and gauze. These data reveal that the gel formulation and the solid SPSS materials are effective inhibitors of the serine proteases elastase & cathepsin G, and the metalloproteases MMP-8 and MMP-9 (FIGS. 10, 11, 12, & 13).

EXAMPLE 7

Application Of Material 18

About 25 Grams Of sodium alginate (Sigma-Aldrich, PO Box 14508, Mo. 63178, UNITED STATES) can be combined with 250 mL of sterile deionized water (as by autoclave sterilization) and the mixture can be autoclaved in order to facilitate dissolution. Simultaneously 15 grams of SPSS (1000K) can be combined with 200 mL of sterile deionized water and autoclaved (to 105° C.) as the above described in order to facilitate dissolution. An alternative method of dissolution utilizes a roller mill (room temperature). Following autoclaving the above solutions can be combined and filtered. Separately, 1 liter of 0.5 M $CaCl_2$ solution in deionized win order to prepare beads. The beads can be allowed to dwell in the calcium chloride solution in deionized water is prepared and 10 grams of SPSS (1000K) added in order to ensure that little SPSS is lost during the cross-linking step. The alginate solution can be added in a drop wise fashion to the $CaCl_2$-SPSS solution and the formed beads are allowed to stir for 5 minutes and subsequently filtered through polyester fabric. The beads can be packaged and refrigerated prior to testing. The calcium PSS-containing beads can be effective at inhibiting elastase (see bar chart) IMS-70-1, IMS-70-2, IMS-70-alginate, and IMS-1000-aliginate (FIG. 14). Similarly the products can be effective against cathepsin G, MMP-8, and MMP-9. With the alginate-SPSS solution from above, a sheet of Evolon (130 grams) soft (Freudenberg/Evolon NA) can be immersed so as to become fully wetted and the fabric removed and excess alginate solution removed. The fabric can be placed into the $CaCl_2$-PSS solution and allowed to dwell until the alginate has become firm. The fabric composite can be cut to size and sterilized by electron beam irradiation (25 kG) prior to studies.

EXAMPLE 8

Application of Material 18 a Dose Response Study of Sodium Polystyrene Sulfonate (SPSS) Inhibition of Neutrophil Elastase Different amounts of SPSS were incubated with 12.5 milliunits of neutrophil elastase in 1.0 mL of buffer for 2 hours at 25° C. Aliquots (160 microliters) were mixed with an elastase specific substrate and the liberation of anilide was monitored spectrophotometrically. Inhibition was rapid and irreversible with the full inhibitory effects observed as fast as the measurements could be made (~5 minute intervals). The rate of inhibition is a consequence of the inhibitor and the proteins being in the solution phase. Dilutions of elastase were used to generate a standard curve and concentrations down to 1 microgram/mL inhibited elastase efficiently (~80%) but not completely (FIG. 15). A comparison of SPSS against con-droitin-6-sulfate (C6S) for the inhibition of elastase revealed that C6S was much less efficient an inhibitor than SPSS. C6S could not achieve the same level of inhibition (only 45%) and it required about 21 times the amount of C6S as SPSS to achieve an equivalent level of inhibition.

EXAMPLE 9

Derivatization of SPSS with Chlorhexidine

Sodium Polystyrene Sulfonate (SPSS, 70,000 mw) acquired from Sigma-Al$^d$rich, PO Box 14508, St. Louis, Mo. 63178, UNITED STATES and purified as described in Example 1 can be dissolved into deionized water to yield a 10-20% solids solution. Separately, chlorhexidine diacetate (Sigma) is added to warm deionized water (35° C.) to yield a 25-30 mmol solution. The chlorhexidine diacetate solution can be added directly to the SPSS solution and a precipitate forms. The precipitate is filtered from the mixture and washed with deionized water. The solid is dried under vacuum to yield an off-white solid.

EXAMPLE 10

Derivatization of SPSS with Doxycyline

Sodium Polystyrene Sulfonate (SPSS, 70,000 mw) acquired from Sigma-Aldrich, PO Box 14508, St. Louis, Mo. 63178, UNITED STATES and purified as described in Example 1 can be dissolved into deionized water to yield a 10-20% solids solution. Separately, doxycycline hydrochloride (Sigma) is dissolved into deionized water (20% w/w) and an equivalent molar amount of doxycycline is added to the SPSS solution. Upon the addition of doxycycline hydrochloride to the SPSS solution, a precipitate forms. Following the complete addition, the lightly yellow-colored solid is filtered, washed with deionized water and dried under vacuum to yield a light yellow solid. The doxycycline is insoluble in deionized water but slowly soluble in the phosphate buffered saline (PBS) aqueous media and the dissolution measured by UV spectroscopy.

EXAMPLE 11

Application of Material 18—Antimicrobial Effectiveness of 14% Ag-PSS

14% silver incorporation (substitution) of SPSS to yield a mixed sodium (86%) silver (14%) compound was tested against *Acinetobacter baumanni, Staphylococcus Aureus*, and *Pseudomonas aeruginosa*. The $MIC_{50}$ and $MIC_{90}$ were determined against all three pathogens. Clinical isolates of *Pseudomonas aeruginosa, Stephylococcus aureus*, and *Acinetobacter baumanni* were grown overnight and then diluted 1:50 in Mueller Hinton broth. Bacteria were incubated overnight with different concentrations of Ag-PSS in 96-well format (n=4/sample). Light scattering (600 nm) was used to measure growth. The data are represented in FIG. 16.

EXAMPLE 12

Application of Material 18 14% PSS Silver Ointment in the Treatment of Full Thickness Burns in the Rat (Comb Burn Model)

Full thickness burn injuries (three—2.0×1.0 cm, 0.5 cm interspace, i.e. the space between burn wounds) were made in the back of an anesthetized animal. The burn wounds were dressed immediately following the burn and redressed each day thereafter. A three pronged brass template heated to 100° C. was used to generate three full thickness burns (1×2 cm) on each side of the spine of Wistar rats (n=6). Each of the burns are separated by two interspaces (0.5×2 cm). Escharotomies were created in the burn sites and the wounds were dressed with an ointment containing 14% Ag-PSS. Contralateral (control) wounds were dressed with vehicle ointment only. A. Representative wounds at day 5-Left side: Ag-PSS ointment, right side: control ointment. B: Quantitation of Preserved Interspace Tissue. The data detailed in FIGS. 17 and 18 reveals that the experimental dressing preserved approximately twice that of the control ointment.

EXAMPLE 13

Application of Material 18—Preparation of 50:50 Polylactide Co-glycolide (50:50 PLGA) SPSS Microspheres for Controlled Release of SPSS Using a Water/Oil/Water Emulsion Technique SPSS as purified in example 1 was dissolved into deionized water to prepare about a 8% w/w solution. Separately, PLGA (50:50, Lactel Polymers) dissolved into dichloromethane to yield a solution of 5% solids. Two solutions are combined (with the total SPSS added representing 8% of the PLGA mass and shaken to form an emulsion. Separately, a 1% polyvinyl alcohol (PVA, 87-89% hydrolyzed) solution is prepared (roughly 30 times the total volume of the (PLGA) dichloromethane-aqueous (SPSS) emulsion. The emulsion is added to the rapidly stirring PVA solution and the mixture slowly heated to 45° C. The mixture was allowed to stir at 45° C. for 60 minutes and the mixture cooled and filtered. The tan colored material in the filter was washed with D-mannitol (2% w/w) and the spheres allowed to dry.

The microspheres were imaged on a hemocytometer grid and found to be very regular in shape (FIG. 19) and size considering that the experiment was carried out using standard laboratory equipment with few controls in place. An evaluation of 25 randomly chosen microspheres from the sample revealed that a mean spherical surface area of 0.0259mm$^2$ (r=45 µm), a median of 0.0258 mm$^2$ (r=45 µm), and a std. dev. of 0.0123 mm$^2$. The minimum and maximum surface areas in the sample were found to be 0.00859 (r=26 µm) and 0.0492 mm$^2$ (r=63 µm) respectively. These surface areas translate to diameters of ca. 90 µm (mean), 52 µm (min) and 126 µm (max). Overall, these data detail a uniform process.

The release of SPSS from the microspheres was followed via UV spectroscopy and total release was shown to require about 5 days in PBS at 37° C.

EXAMPLE 14

Preparation of Material 18 Silver Chondroitin-6-Sulfate (Ag-C6S) Using Silver Acetate Sodium chondroitin-6-sulfate (C6S, 1.5 mmole, shark cartilage source, Seikagaku, Japan) was added to a small beaker as received and 20 mL of deionized water was added. The mixture was stirred until dissolved at room temperature and 1.5 mmole of silver acetate (250.37 mg, Fluka) were added and allowed to stir until completely dissolved. To the stirring solution an additional 1.5 mmole of sodium chondroitin sulfate was added and allowed to stir until completely dissolved. The mixture was filtered, placed in a lyophilization vessel, frozen and lyophilized to yield about 2.2 grams of 50% substituted Ag-C6S as a flocculent grayish solid. The Ag-C6S was very soluble at 50 mol % and 100 mol % substitution. The byproduct sodium acetate was not removed but may be dialyzed away as needed.

Using a mass balance approach to determining the amount of silver incorporated, silver was precipitated as silver chloride, isolated, dried and weighed. Incorporation was determined to be approximately 50 mol %.

EXAMPLE 15

Preparation of Material 18 Mixed Sodium/Silver Chondroitin-6-Sulfate (Na/Ag-C6S) Using Silver Ion Modified Dowex Mac-3 Resin The Mac-3 resin (Dow Chemical) was stirred with 1.0 N NaOH solution in deionized water for 1 hour and the resin filtered, washed and re-suspended in deionized water. While stirring with a mechanical stirrer, silver acetate (Fluka) was added to the mixture and dissolution of the silver acetate followed. The silver-modified Dowex MAC-3 was triturated with cold deionized water to remove any insoluble matter and filtered under vacuum. The resin was rinsed with isopropanol and allowed to dry in the absence of light.

Sodium chondroitin-6-sulfate (Seikagaku, Japan) was dissolved into deionized water and mechanically stirred. A 10× (w/w) amount of the silver-modified Dowex MAC-3 was added and the mix heated to 50° C. and stirred for 2 hours. The resin was filtered and washed with deionized water and the filtrate transferred to a lyophilizer vessel and frozen. The frozen solution was placed on a lyophilizer for 72 hours to yield a light gray fibrous solid. Silver chloride was precipitated by the addition of saline to a solution of the Ag-C6S. The AgCl was dried onto the preweighed filter paper and weighed. Silver incorporation was determined to be 29% by mass balance. More or less silver incorporation can be achieved by varying the amount of silver-modified Dowex MAC-3, for a given amount of starting C6S, up or down respectively.

EXAMPLE 16

Preparation of Material 18 Arginine Chondroitin-6-Sulfate (C6S-Arg)

Sodium chondroitin-6-sulfate (C6S, 1.5 mmole, shark cartilage source, Seikagaku, Japan) was added to a small beaker as received and 20 mL of deionized water was added.

Separately, arginine base (1.5 mmole, Sigma) in deionized water (10 mg/mL) is added to account for an equimolar quantity of sodium chondroitin sulfate and the solution stirred for 1 hour at room temperature. The solution is transferred into a lyophilizer container and frozen. The frozen mass is placed under vacuum of the lyophilizer and the solid polystyrene arginine sulfonate is isolated as a flocculent off-white solid.

The invention claimed is:

1. A composition for the healing of a multicellular organism, the composition comprising at least one polysulfonated material, the polysulfonated material being insoluble in deionized water and soluble in ion-comprising aqueous media, wherein the polysulfonated material comprises a polystyrene sulfonate, the polystyrene sulfonate comprising one or more of polystyrene arginine sulfonate, polystyrene mafenide sulfonate, silver substituted polystyrene sulfonate, chlorhexidine substituted polystyrene sulfonate, and/or doxycycline substituted polystyrene sulfonate.

2. The composition of claim 1, wherein the polysulfonated material comprises a backbone that includes at least one repeating unit that is chiral.

3. The composition of claim 1, wherein the polysulfonated material comprises an achiral backbone.

4. The composition of claim 1, wherein the polysulfonated material is chiral, the chirality being imparted by a chiral pendant group substitution.

5. The composition of claim 1, wherein the polysulfonated material further comprises at least one of a proteoglycan, the proteoglycan comprising one or more of dermatan sulfate, keratan sulfate, aggrecan, neurocan, brevican, versican, decorin, biglycan, fibromodulin, keratocan, osteoglycin and/or lumican.

6. The composition of claim 1, wherein the polysulfonated material comprises at least two sulfonate groups modified to sulfonamides, the sulfonamides configured to cross-link at least one portion of the polysulfonated material with another portion of the polysulfonated material.

7. The composition of claim 1, further comprising a solid matrix material.

8. The composition of claim 7, wherein the matrix material comprises biodegradable material.

9. The composition of claim 7, wherein the matrix material is a non-biodegradable-biomedical material comprising at least one of a silicone, a polyurethane, a polyalkylene, a hydrogel, or a polyester.

10. The composition of claim 1, further comprising at least one of an antimicrobial agent, antibacterial metal cation, angiogenic agent, antifungal agent, antiviral agent, antiparasitic agent, anesthetic, enzyme, enzyme inhibitor, growth factor, anti-inflammatory agent, antihistamine, analgesic, antineoplastic agent, hormone, cytotoxic agent, tranquilizer, a proteoglycan, a glycosaminoglycan, silver cation, nutrient, vitamin, amino acid, nucleic acid, protein, peptide, cytokine, monoclonal antibody, and antiangiogenic agent.

11. The composition of claim 1 formulated as a gel, paste, cream, solution, ointment, or lotion.

12. The composition of claim 1 formulated as an amorphous hydrogel, the sulfonated material being blended into the hydrogel formulation.

13. The composition of claim 1 further comprising collagen or gelatin.

14. A composition for the healing of a multicellular organism, the composition comprising at least one polysulfonated material, the polysulfonated material being insoluble in deionized water and soluble in ion-comprising aqueous media, wherein the polysulfonated material comprises a chondroitin sulfate, the chondroitin sulfate comprising one or more of silver chondroitin-6-sulfate, sodium/silver chondroitin-6-sulfate, and/or arginine chondroitin-6-sulfate.

* * * * *